United States Patent
Yamagata et al.

(10) Patent No.: US 10,765,407 B2
(45) Date of Patent: Sep. 8, 2020

(54) ULTRASOUND DIAGNOSIS APPARATUS

(71) Applicant: Toshiba Medical Systems Corporation, Otawara-shi (JP)

(72) Inventors: Hitoshi Yamagata, Otawara (JP); Yasuhiko Abe, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 816 days.

(21) Appl. No.: 14/662,469

(22) Filed: Mar. 19, 2015

(65) Prior Publication Data

US 2015/0216509 A1  Aug. 6, 2015

Related U.S. Application Data

(63) Continuation of application No. PCT/JP2013/077179, filed on Oct. 4, 2013.

(30) Foreign Application Priority Data

Oct. 4, 2012 (JP) ................................. 2012-222592

(51) Int. Cl.
*A61B 8/12* (2006.01)
*A61B 8/00* (2006.01)
(Continued)

(52) U.S. Cl.
CPC .............. *A61B 8/5223* (2013.01); *A61B 8/06* (2013.01); *A61B 8/065* (2013.01); *A61B 8/08* (2013.01);
(Continued)

(58) Field of Classification Search
CPC ............................ A61B 8/5223; A61B 8/4483
See application file for complete search history.

(56) References Cited

U.S. PATENT DOCUMENTS 5,515,849 A * 5/1996 Murashita ............. A61B 8/488
600/479
5,795,296 A * 8/1998 Pathak ................ A61B 5/1075
600/443

(Continued)

FOREIGN PATENT DOCUMENTS

CN  1777898 A  5/2006
CN  101744644 A  6/2010
(Continued)

OTHER PUBLICATIONS

English translation of International Search Report dated Nov. 5, 2013 for PCT/JP2013/077179 filed on Oct. 4, 2013.
(Continued)

*Primary Examiner* — Jeffrey G Hoekstra
*Assistant Examiner* — Jason M Ip
(74) *Attorney, Agent, or Firm* — Oblon, McClelland, Maier & Neustadt, L.L.P.

(57) ABSTRACT

An ultrasound diagnosis apparatus includes an ultrasound transducer, an evaluation value acquisition unit, a determination unit, and an output unit. The evaluation value acquisition unit obtains an evaluation value for evaluating the function of tissue including a predetermined site based on biological information acquired for a predetermined period of time by the ultrasound transducer. The determination unit determines whether the function of the tissue is abnormal based on the evaluation value. The output unit outputs information based on a result of determination by the determination unit.

14 Claims, 28 Drawing Sheets

(51) Int. Cl.
- *A61B 8/06* (2006.01)
- *A61B 8/14* (2006.01)
- *A61B 8/08* (2006.01)

(52) U.S. Cl.
CPC .............. *A61B 8/0883* (2013.01); *A61B 8/12* (2013.01); *A61B 8/145* (2013.01); *A61B 8/4444* (2013.01); *A61B 8/4483* (2013.01); *A61B 8/4494* (2013.01); *A61B 8/463* (2013.01); *A61B 8/466* (2013.01); *A61B 8/488* (2013.01); *A61B 8/5207* (2013.01); *A61B 8/5292* (2013.01); *A61B 8/54* (2013.01); *A61B 8/543* (2013.01); *A61B 8/483* (2013.01)

(56) References Cited

U.S. PATENT DOCUMENTS

| | | |
|---|---|---|
| 2003/0032880 A1 | 2/2003 | Moore |
| 2003/0139661 A1* | 7/2003 | Kimchy ................ A61B 1/041 600/407 |
| 2006/0036176 A1* | 2/2006 | Angelsen ................ A61B 8/12 600/459 |
| 2007/0129625 A1 | 6/2007 | Li et al. |
| 2007/0239014 A1 | 11/2007 | Yoshikawa et al. |
| 2011/0144501 A1 | 6/2011 | Nishimura |
| 2011/0257529 A1 | 10/2011 | Casciaro et al. |
| 2012/0101383 A1* | 4/2012 | Hyun .................... A61B 5/1072 600/443 |
| 2012/0150024 A1 | 6/2012 | Amit et al. |
| 2012/0237098 A1 | 9/2012 | Rognin et al. |

FOREIGN PATENT DOCUMENTS

| | | |
|---|---|---|
| CN | 101953696 A | 1/2011 |
| CN | 102088913 A | 6/2011 |
| CN | 102123667 A | 7/2011 |
| CN | 102223842 A | 10/2011 |
| CN | 102309342 A | 1/2012 |
| CN | 102483847 A | 5/2012 |
| JP | 2003-325521 A | 11/2003 |
| JP | 2007-222253 A | 9/2007 |
| JP | 2009-516576 A | 4/2009 |
| WO | WO 03/094737 A1 | 11/2003 |

OTHER PUBLICATIONS

Combined Office Action and Search Report dated May 5, 2016 in Chinese Patent Application No. 201380052080.9 with English translation of category of cited documents.

Combined Chinese Office Action and Search Report dated Mar. 3, 2017 in Patent Application No. 201380052080.9 (with English translation of Categories of Cited Documents).

* cited by examiner

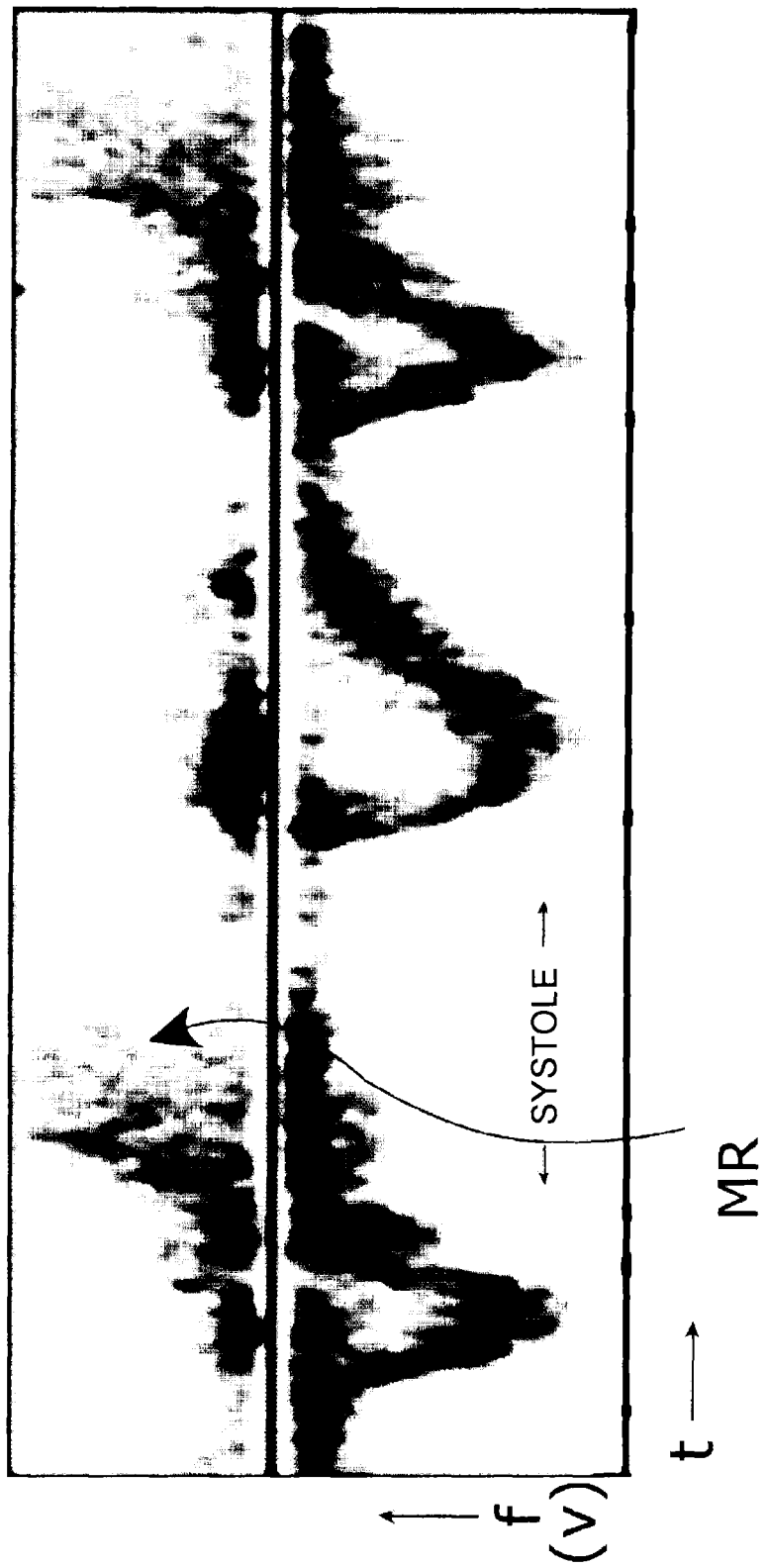

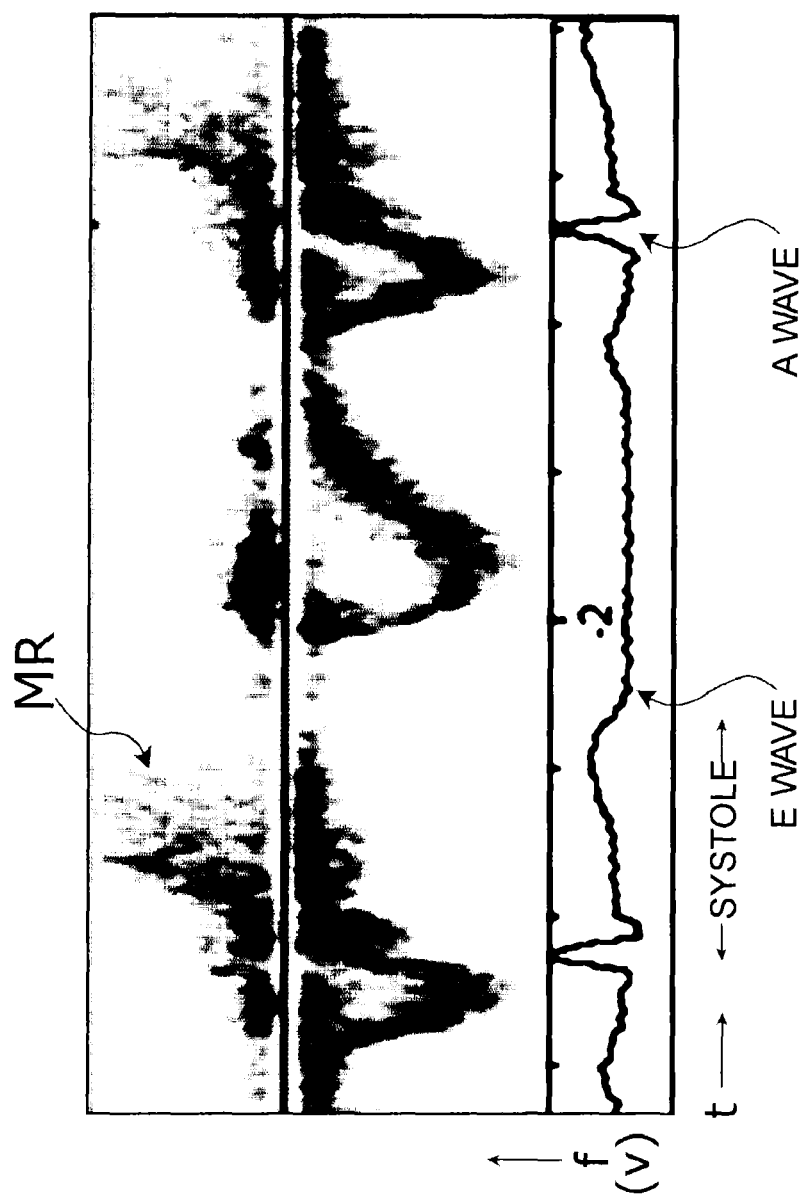

end-diastole    end-systole $$\text{RadialStrain} = \frac{(L_r - L_0)}{L_0} \times 100 [\%] \quad \cdots (1)$$

$$\text{Radial 3D Strain} = \frac{(L - L_0)}{L_0} \times 100 [\%] \quad \cdots (2)$$

ns apparatus

ULTRASOUND DIAGNOSIS APPARATUS

CROSS-REFERENCE TO RELATED APPLICATION

This application is based upon and claims the benefit of priority from Japanese Patent Application No. 2012-222592, filed Oct. 4, 2012; the entire contents of which are incorporated herein by reference.

FIELD

Embodiments described herein relate generally to an ultrasound diagnosis apparatus.

BACKGROUND

A medical image diagnosis apparatus is a device that creates, for examination and diagnosis, a medical image (tomographic image, blood flow image, etc.) from information on tissues in a subject without surgical removal of the tissues. Examples of such medical image diagnosis apparatus include X-ray diagnosis apparatuses, X-ray CT (Computed Tomography) apparatuses, MRI (Magnetic Resonance Imaging) apparatuses, and ultrasound diagnosis apparatuses.

From medical images, anatomical images representing the form of tissue inside the subject's body and functional images representing the function of tissue inside the subject's body are generated. A variety of medical images are generated according to the physical condition of the subject and the status of the disease, and used to support diagnosis, surgery, treatment, and the like. For example, medical images are sometimes used in the continuous monitoring of the subject. In the ultrasound diagnosis apparatus, medical images may be used for the monitoring of blood flow and cardiac function such as, for example, the monitoring of moving objects such as myocardium and blood flow in the heart, and the like.

To monitor the function of tissues in the subject's body using medical images, there may be a need to continue capturing images of the tissues for a certain period of time. Besides, to acquire the condition of a single tissue, it may be required to capture medical images from several points of view. Images generated in such imaging are displayed for a prolonged period of time, or contain a large amount of information (a large number of images, etc.). If the workload of imaging and reading the images (interpretation, etc.) increases, it may become difficult to monitor the conditions of body tissues.

BRIEF DESCRIPTION OF THE DRAWINGS

FIG. 7A is a schematic diagram of an example of a Doppler spectrum image generated by the generating unit of the first embodiment;

FIG. 7B is a schematic diagram of an example of ECG (electrocardiogram) waveform and the Doppler spectrum image generated by the generating unit of the first embodiment;

DETAILED DESCRIPTION

In general, according to one embodiment, an ultrasound diagnosis apparatus includes an ultrasound transducer (ultrasound probe), an evaluation value acquisition unit, a determination unit, and an output unit. The ultrasound transducer transmits and receives ultrasound waves while being inserted in a subject to acquire biological information of a predetermined site of the subject. The evaluation value acquisition unit obtains an evaluation value for evaluating the function of tissue including the predetermined site based on the biological information acquired for a predetermined period of time by the ultrasound transducer. The determination unit determines whether the function of the tissue is abnormal based on the evaluation value. The output unit outputs information based on a result of determination by the determination unit.

Referring to FIGS. 1 to 19, a description is given of an ultrasound diagnosis apparatus according to first to seventh embodiments.

First Embodiment

Overview

Described below is an overview of an ultrasound diagnosis apparatus 100 according to the first embodiment. The ultrasound diagnosis apparatus 100 first captures images of the subject in the normal condition, and generate a moving image of anatomical images (B-mode image, MPR (Multi-Planar Reconstruction) image, etc.). The ultrasound diagnosis apparatus 100 then performs anatomical evaluation (calculation of left ventricular volume, etc.) from the form of body tissues of the subject, and the like represented in the moving image. The evaluation is calculated as an evaluation value (numerical information). The ultrasound diagnosis apparatus 100 uses the evaluation value obtained in the normal condition as reference evaluation value for abnormality determination process (described later). The normal condition is determined based on biological information received from a biological information measuring unit 120 (see FIG. 5). For example, the biological information measuring unit 120 obtains biological information (electroencephalogram, electromyogram, electrocardiogram, eye movement, respiration, pulse wave, etc.) from the subject, and sends it to a main body 101. As another example, the normal condition may be determined based on the evaluation (functional or anatomical evaluation) of an ultrasound image captured by the ultrasound diagnosis apparatus 100.

After obtaining the reference evaluation value in the normal condition, the ultrasound diagnosis apparatus 100 captures images of the subject for a predetermined period of time, and generates a moving image of anatomical images. Then, in the same manner as the evaluation of the reference evaluation value, the ultrasound diagnosis apparatus 100 performs anatomical evaluation of a form indicated by the moving image. The evaluation is performed over time, and an evaluation value is sequentially calculated. The evaluation value sequentially calculated is referred to as "compared evaluation value".

Figure 5:
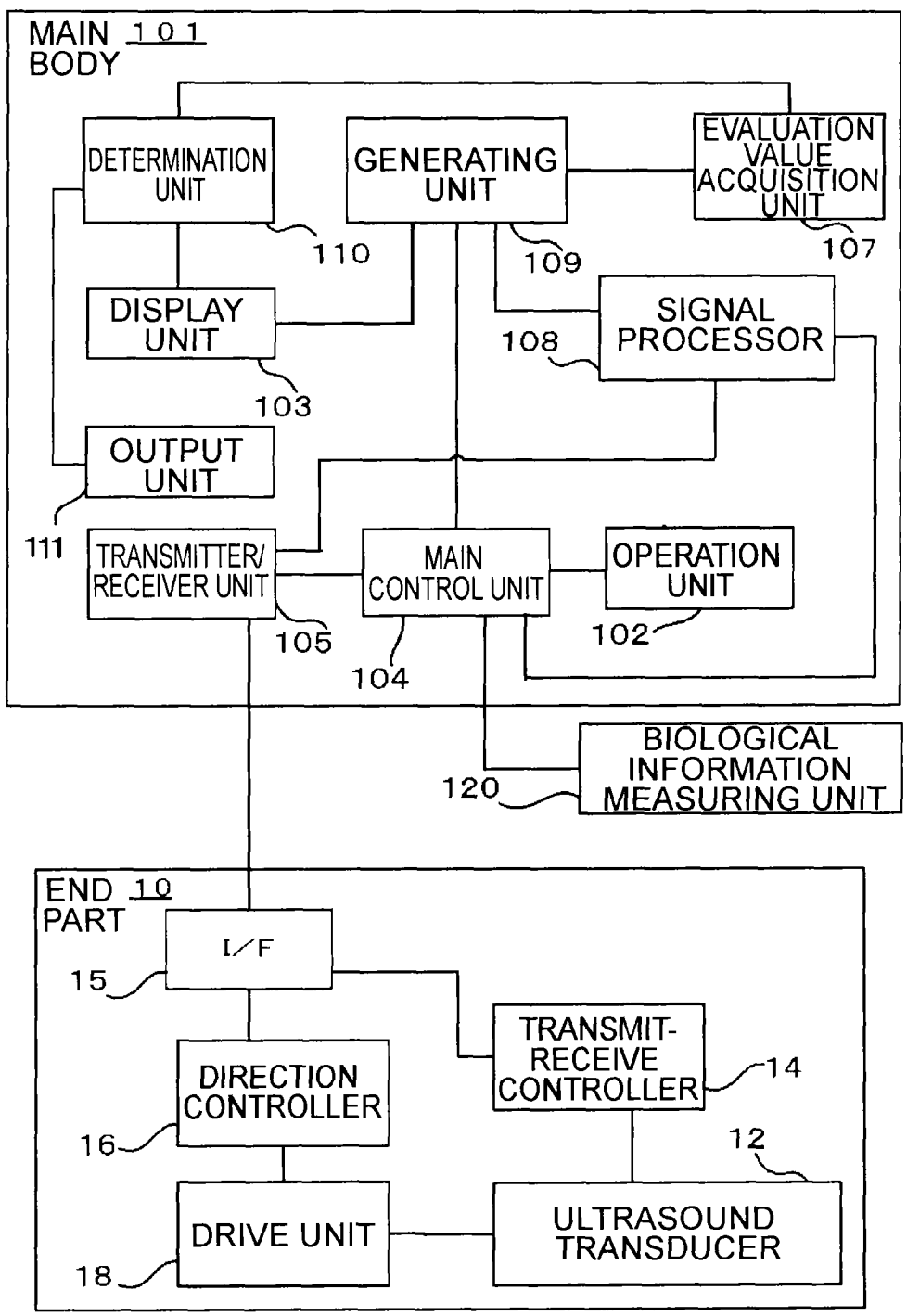
FIG. 5 is a schematic block diagram illustrating an example of the functional structure of a main body of the ultrasound diagnosis apparatus of the first embodiment.

The compared evaluation value sequentially calculated is compared to the reference evaluation value (an evaluation value acquisition unit 107; see FIG. 5). A comparison result between the compared evaluation value and the reference evaluation value is an example of a "comparison result". If the comparison result between the compared evaluation value and the reference evaluation value is within a predetermined range set in advance, the ultrasound diagnosis apparatus 100 determines that it is "normal" (a determination unit 110; FIG. 5). On the other hand, if the comparison result is outside the predetermined range, the ultrasound diagnosis apparatus 100 outputs information indicating abnormal (an output unit 111; FIG. 5).

<External Structure>

Figure 1:
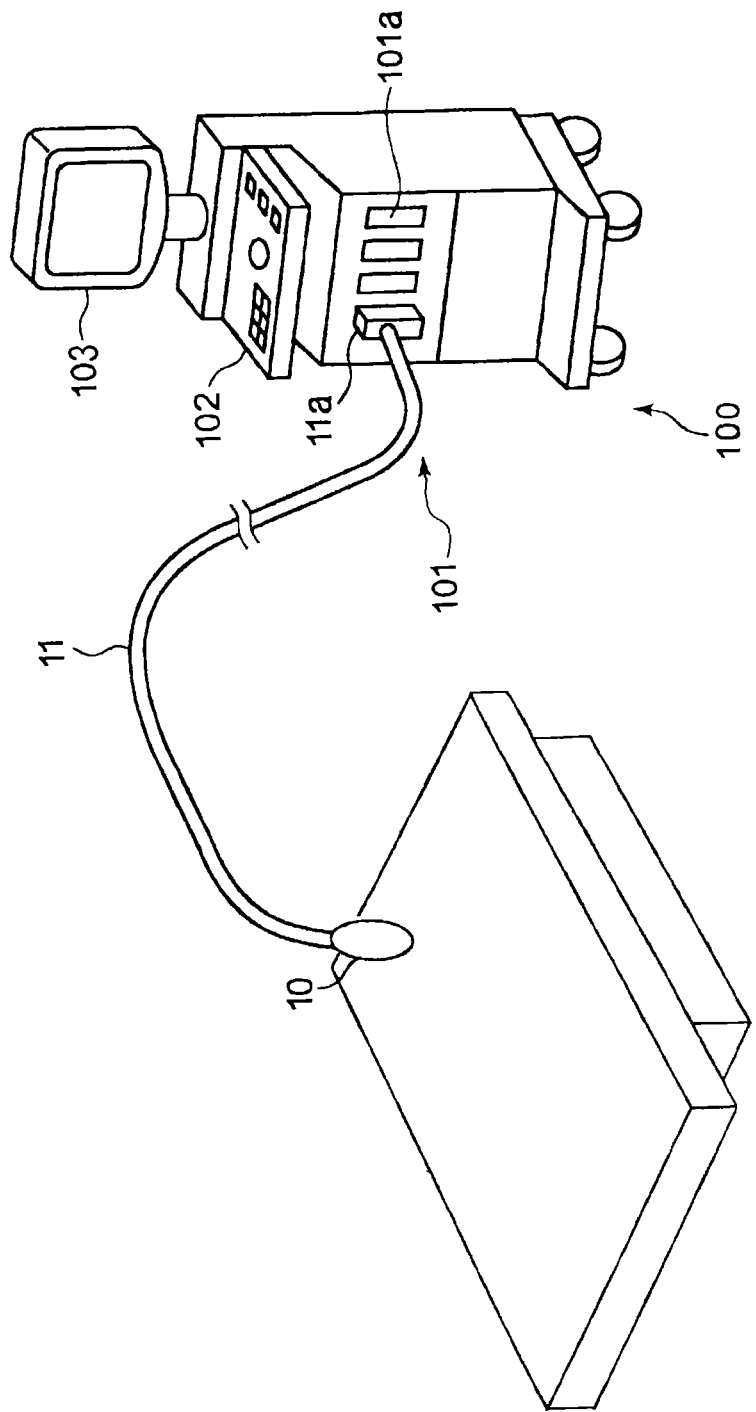
FIG. 1 is a schematic perspective view of an ultrasound diagnosis apparatus.

The overview of the overall structure of the ultrasound diagnosis apparatus 100 according to the first embodiment is described first with reference to FIG. 1. FIG. 1 is an external view of the ultrasound diagnosis apparatus 100 for explaining the overview of its structure.

As illustrated in FIG. 1, the ultrasound diagnosis apparatus 100 of the embodiment includes the main body 101, an end part 10, and the like. The end part 10 and the main body 101 are connected through a cable 11. In the example of FIG. 1, a connector 11a is provided to the end of the cable 11. The main body 101 is provided with connection parts 101a. The connection parts 101a are formed to be connectable to the connector 11a. The main body 101 includes an operation unit 102 and a display unit 103. The operation unit 102 is used to operate the ultrasound diagnosis apparatus 100. The display unit 103 displays an image generated by the ultrasound diagnosis apparatus 100 and other images. Incidentally, the illustration of the ultrasound diagnosis apparatus 100 in FIG. 1 is by way of example only. The structure of the main body 101, the arrangement and the structure of the cable 11, the operation unit 102 and the display unit 103, and the like are not limited to those in FIG. 1, and susceptible to various modifications as appropriate. For example, instead of being configured as illustrated in FIG. 1, the main body 101 may be configured as a portable ultrasound diagnosis apparatus.

<Structure of End Part>

Figure 2A:
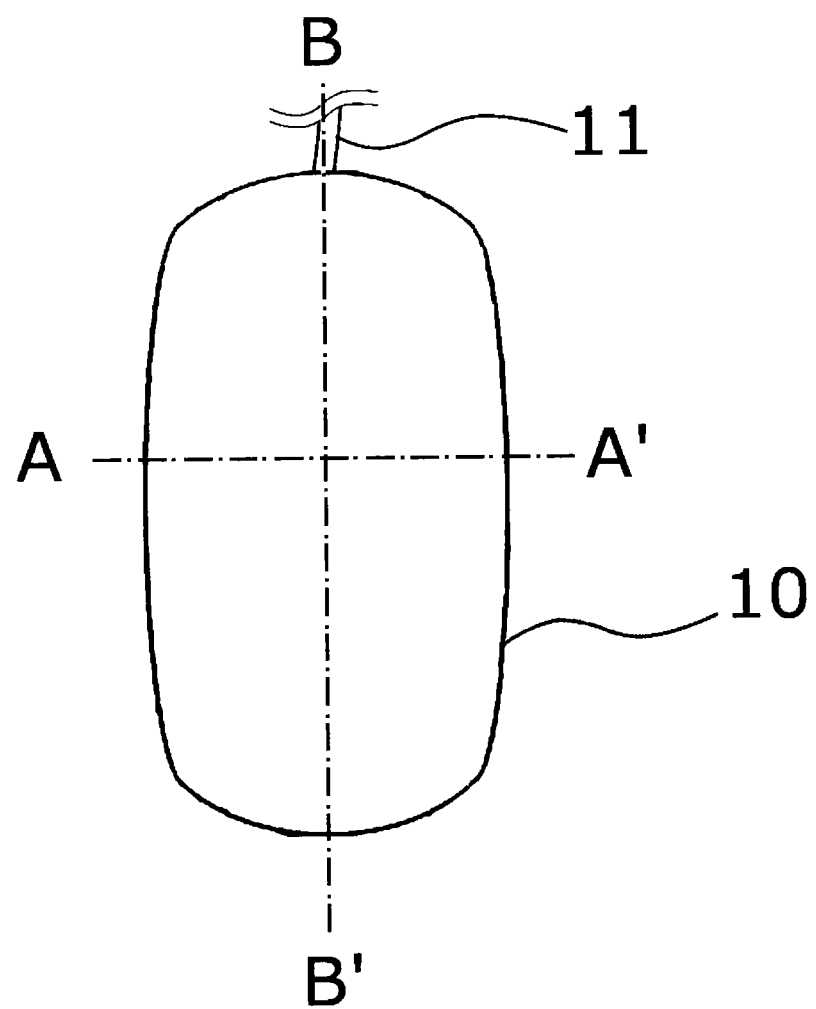
FIG. 2A is a schematic side view of an end part.
Figure 2B:
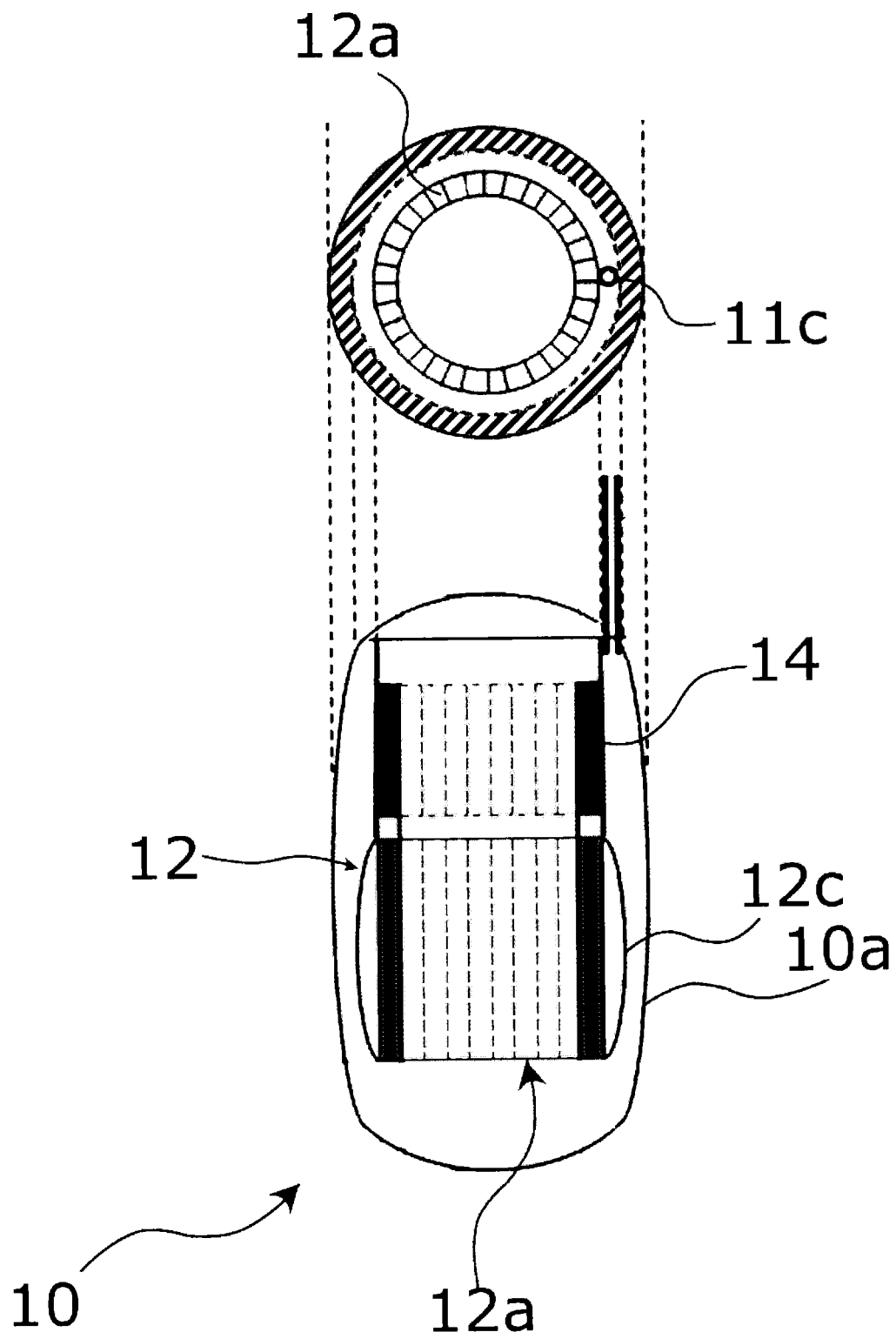
FIG. 2B provides schematic cross sections taken along lines A-A' and B-B' in FIG. 2A, illustrating the positional relationship of parts therein.
Figure 3A:
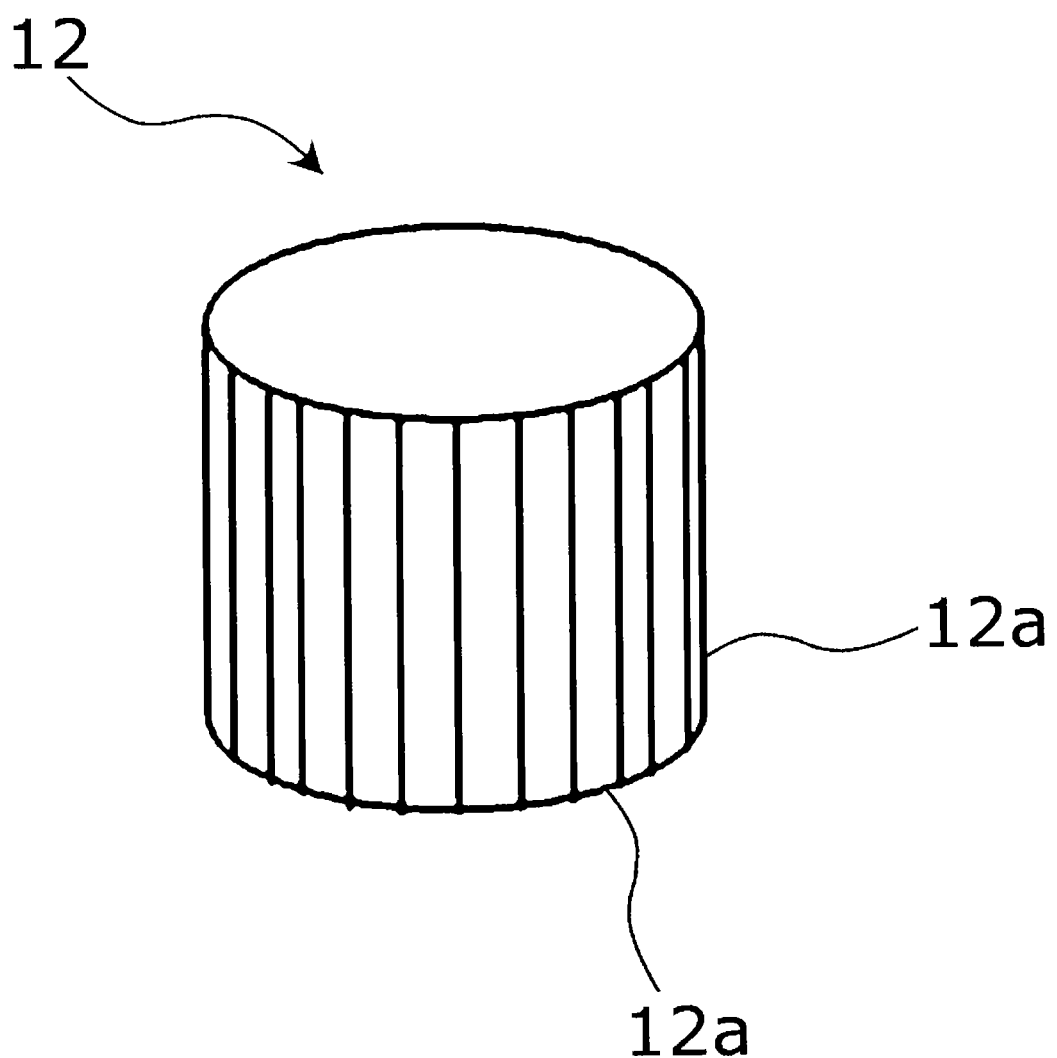
FIG. 3A is a schematic perspective view of the ultrasound transducer.

In the following, the structure of the end part 10 is described with reference to FIGS. 2A, 2B, and 3A. FIG. 2A is a schematic side view of the end part 10. FIG. 2B provides schematic cross sections taken along lines A-A' and B-B' in FIG. 2A, and illustrates the positional relationship of parts therein. In FIG. 2B, the cable 11, a direction controller 16, and a drive unit 18 are not illustrated. FIG. 3A is a schematic perspective view of an ultrasound transducer 12, which is a one-dimensional (1D) transducer array where ultrasound oscillators 12a are provided all over the outer peripheral surface of a support.

(Overview of End Part)

In the examples of FIGS. 1 and 2A, the end part 10 in a capsule form is used as a device for transmitting/receiving ultrasound waves. As illustrated in FIG. 2B, the end part 10 includes a container 10a formed in an ellipsoid. The container 10a includes therein the ultrasound transducer 12, a transmit-receive controller 14, an interface (I/F) 15, and the like (see FIG. 4). The direction controller 16 and the drive unit 18 may be provided inside the container 10a. FIG. 2B does not illustrate the direction controller 16 and the drive unit 18 of this case. The main body 101 may be referred to as an external device with respect to the container 10a.

As illustrated in FIG. 2B, in the ellipsoidally formed end part 10, for example, the cable 11 is connected to one longitudinal end of the container 10a. A power supply line for supplying power to the end part 10 and a signal line in the cable 11 run through the inside of the container 10a. These lines are connected to the transmit-receive controller 14, the direction controller 16, and the drive unit 18. As described below, when the container 10a is configured to be placed on tissue in the subject's body, the cable 11 can be configured to prevent the end part 10 from moving in the subject's body. For example, a part of the cable 11 may be fixed to a fixing part (not illustrated) that is fixed to a part of the tissue in the subject's body. Examples of the fixing part include a mouthpiece worn by the subject. By providing a mouthpiece with the fixing part, the extent to which the cable 11 is inserted into the subject's body can be kept within a predetermined range. Thus, the end part 10 can be stayed in the subject's body.

For another example, the container 10a of the end part 10 may be configured to expand so that it is appressed to the body tissue of the subject such as the esophagus. By appressing the container 10a to the body tissue, the end part 10 can be stayed at the body tissue. Although not illustrated, in such a configuration, the container 10a is formed to have a double-bag structure. The ultrasound transducer 12 is placed in the inner bag of the container 10a. The outer bag of the container 10a is connected to the cable 11. The cable 11 is communicated with the outer bag, so that fluid, i.e., liquid such as sterile water and the like, can be injected from a pipe 11c (see FIG. 2B) in the cable 11. The container 10a expands with the injection of fluid, and contracts when the fluid is discharged. While the ultrasound transducer 12 is provided in the container 10a of the end part 10, whether other elements, such as the transmit-receive controller 14, the direction controller 16, the drive unit 18, and the like are provided to the end part 10 is determined as appropriate depending on the structure of the ultrasound transducer 12 (element array, etc.).

(Structure of Entire Ultrasound Transducer and Each Component)

The ultrasound transducer 12 as illustrated in the example of FIG. 2B includes the rectangular ultrasound oscillators 12a, which are arranged in a circular array, i.e., 1D array (see FIG. 3A). In the ultrasound transducer 12, the ultrasound oscillators 12a are arranged all over the outer peripheral surface of the support (not illustrated). Hereinafter, the structure, where a backing layer, a piezoelectric element, a front electrode, a back electrode, and an acoustic matching layer on the support are arranged in layers, is referred to as the "ultrasound oscillators" 12a. In addition, a group of the support, the ultrasound oscillators 12a, and an acoustic lens 12c is referred to as the "ultrasound transducer" 12. The support (not illustrated) supports the ultrasound oscillators 12a. The support is, for example, formed in a cylinder, the inside of which is hollow along the central axis. The support may have a columnar form. If all the ultrasound oscillators 12a are required to be tilted to change the transmission direction of ultrasound waves (ultrasound beam angle, etc.), the support is connected to the drive unit 18. The ultrasound oscillators 12a are configured with the backing layer, the piezoelectric element, the front electrode, the back electrode, and the acoustic matching layer arranged radially in layers from the outer peripheral surface of the support toward the outside.

The piezoelectric element (not illustrated) is provided with the back electrode on a surface on the side of the backing layer (on the side of the support), and the front electrode on a surface on the opposite side (the side of the acoustic lens). The piezoelectric element converts a voltage applied to the front electrode and the back electrode into ultrasound waves. The ultrasound waves are transmitted to the subject. Having received reflected waves from the subject, the piezoelectric element converts the waves into voltage (echo signal). The piezoelectric element is generally made of such material as PZT (piezoelectric zirconate titanate/lead zirconate titanate/Pb(Zr,Ti)$O_3$). As the piezoelectric element, PVDF (polyvinylidene difluoride/polyvinylidene fluoride/($CH_2CF_2$)n) may be used. The use of a PVDF film as a piezoelectric element facilitates making the end part 10 because of its flexibility. Further, the ultrasound oscillators 12a can be thinner in the layer direction, and thus the end part 10 can be downsized. Moreover, PVDF films possess good resistance to shock. As for other examples of the piezoelectric element, barium titanate (BaTi$O_3$), PZNT (Pb($Zn_{1/3}Nb_{2/3}$)$O_3$—PbTi$O_3$) single crystal, PMNT (Pb($Mg_{1/3}Nb_{2/3}$)$O_3$—PbTi$O_3$) single crystal, and the like may be used. The piezoelectric element may be of a single layer, or it may be multilayered.

Part of all the piezoelectric elements may be used as pyroelectric elements and connected to a temperature sensing circuit (not illustrated). The temperature sensing circuit detects the temperature around the ultrasound oscillators 12a based on a pyroelectric voltage value or a pyroelectric current value received from the pyroelectric element. The temperature sensing circuit may be located in the end part 10, or in the main body 101. Since the end part 10 is placed in the subject's body, it is effective in monitoring an observation site to enable the operator to know the temperature around the ultrasound oscillators 12a.

The acoustic matching layer is arranged adjacent to the acoustic lens 12c side in the front electrode of the piezoelectric element. That is, the acoustic matching layer is located between the piezoelectric element and the acoustic lens 12c. The acoustic matching layer matches acoustic impedance between the piezoelectric element and the subject. There may be two or more acoustic matching layers arranged in the layer direction. In this case, materials that vary in acoustic impedance in stages are used for the acoustic matching layers. This structure achieves acoustic matching by changing acoustic impedance in stages between the piezoelectric element and the acoustic lens 12c.

The backing layer is arranged adjacent to the support side in the back electrode of the piezoelectric element. The backing layer absorbs ultrasound waves emitted to the opposite direction to their irradiation direction (backward) during ultrasound transmission, thereby suppressing the excessive oscillation of the piezoelectric element. The backing layer suppresses the reflection of ultrasound waves from the back surface of the piezoelectric element when the piezoelectric element is oscillating. Therefore, with the backing layer, it is possible to avoid adverse effect on transmitting/receiving of ultrasound waves. As the backing layer, based on the features including acoustic attenuation, acoustic impedance, and the like, any materials such as an epoxy resin containing PZT powder, tungsten powder, etc., rubber filled with polyvinyl chloride and/or ferrite powder, or porous ceramic impregnated with resin such as epoxy, and the like may be used.

<Acoustic Lens>

The acoustic lens 12c (see FIG. 2B) converges transmitted/received ultrasound waves and forms them into a beam shape. The acoustic lens 12c is made of such material as silicone having an acoustic impedance similar to the living body. If the ultrasound oscillators 12a are in a 2D array, and the ultrasound transducer 12 is capable of converging ultrasound waves into a beam by electronic scanning, the ultrasound transducer 12 may not include the acoustic lens 12c.

Figure 2C:
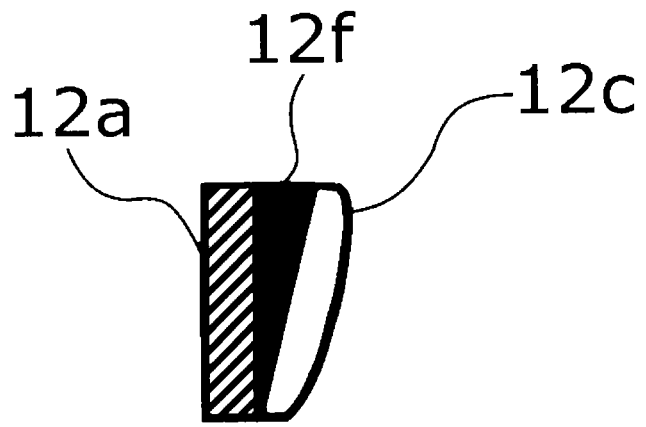
FIG. 2C is a schematic cross section of an ultrasound transducer illustrated in FIG. 2A, to which offset is applied.

When the end part 10 is inserted in the esophagus of the subject and the transmission direction of ultrasound waves is pointed to the heart, a wedge-shaped offset 12f may be added between the acoustic lens 12c and the ultrasound oscillators 12a as illustrated in FIG. 2C. By the addition of the offset 12f, the acoustic lens 12c is tilted to the support of the ultrasound oscillators 12a. With this structure, directions of ultrasound waves from the piezoelectric elements are converged into a different direction. Depending on the tilt angle of the offset 12f, it becomes unnecessary to perform drive control for transmitting ultrasound waves from the ultrasound oscillators 12a of the end part 10 placed in the esophagus to the heart. Alternatively, depending on the tilt angle, the drive control can be simplified.

In the structure illustrated in FIG. 3A, the direction controller 16 and the drive unit 18 (described later) tilt the ultrasound transducer 12 in response to an instruction signal on the transmission direction of ultrasound waves from the main body 101. If the offset 12f is provided, the tilting operation may not be necessary.

(Other Examples of Ultrasound Transducer)

Figure 3B:
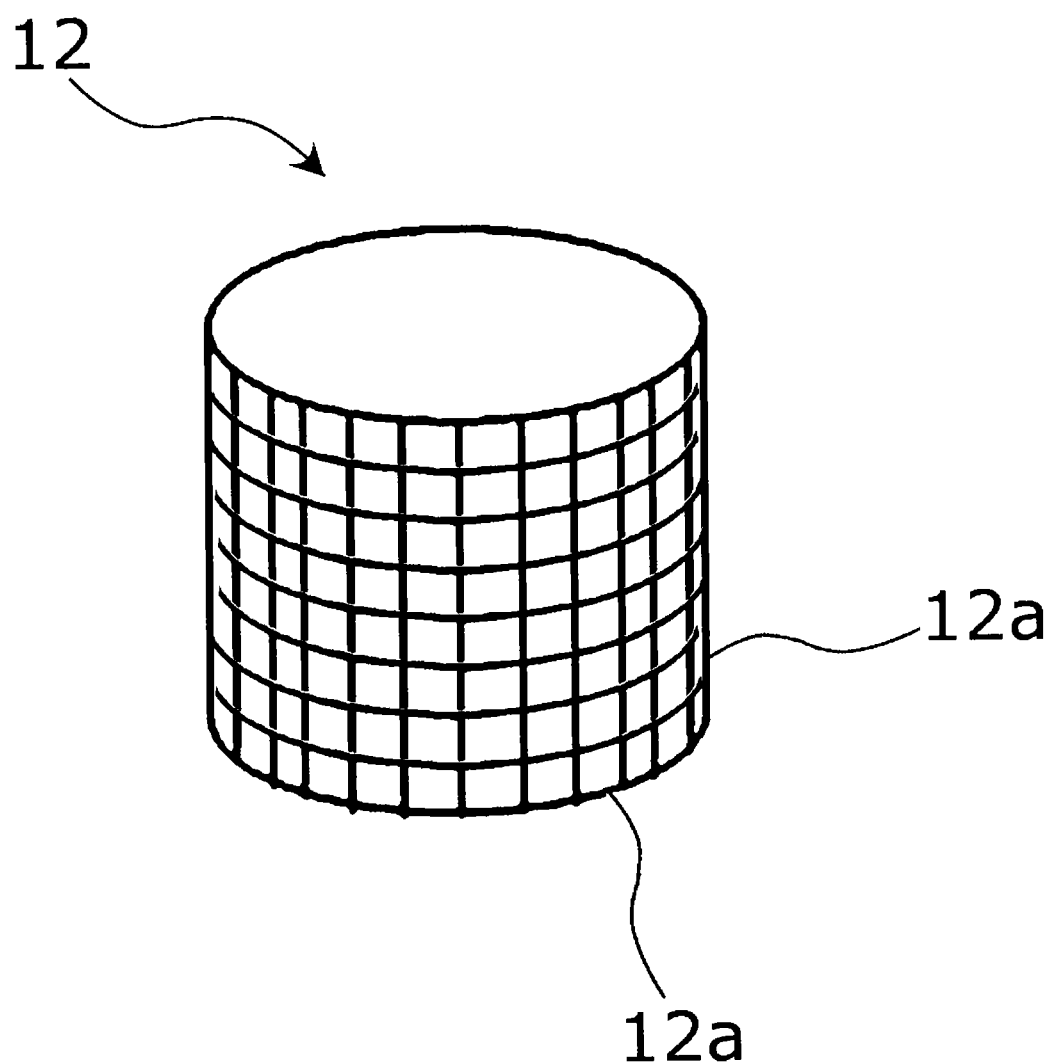
FIG. 3B is a schematic perspective view of the ultrasound transducer.
Figure 3C:
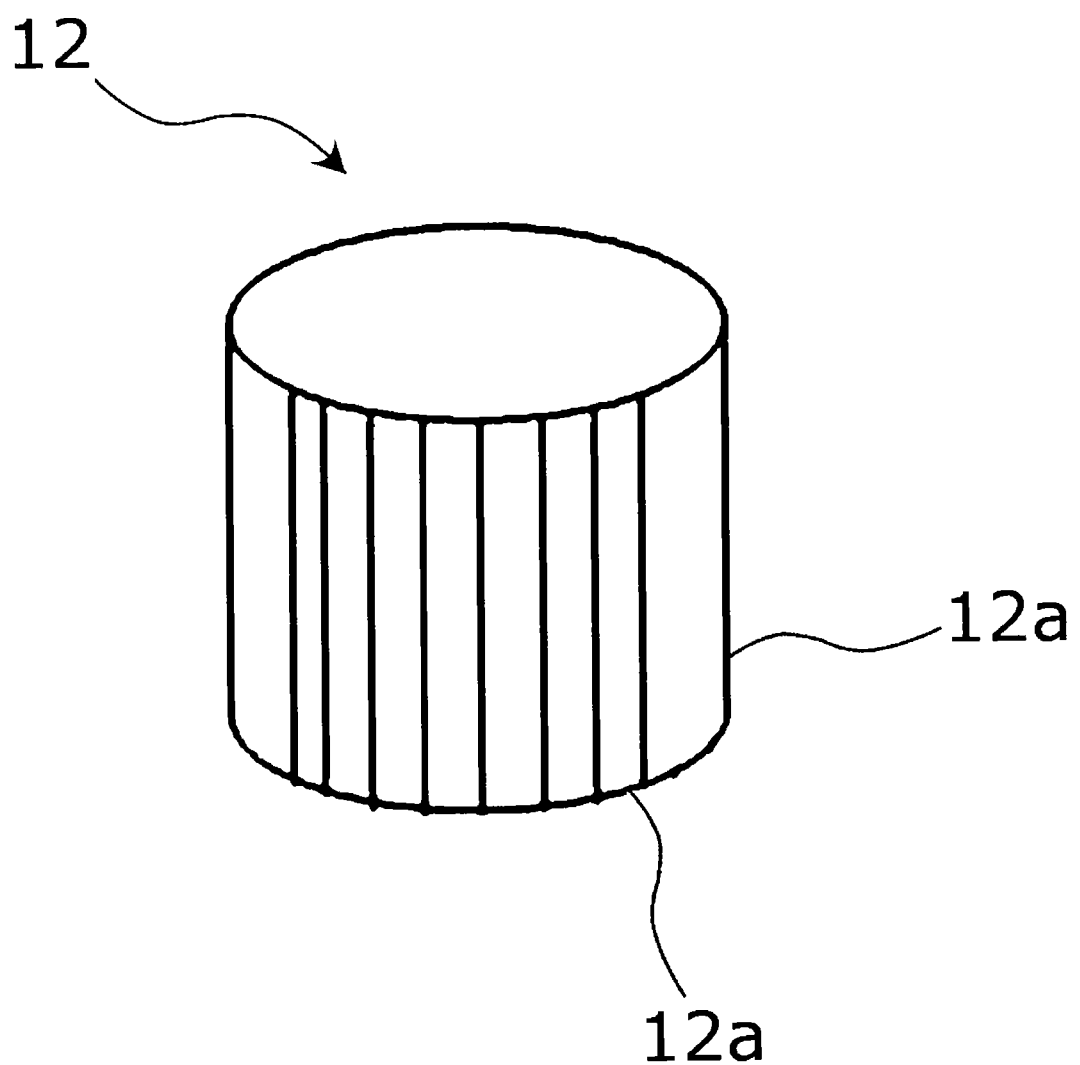
FIG. 3C is a schematic perspective view of the ultrasound transducer.
Figure 3D:
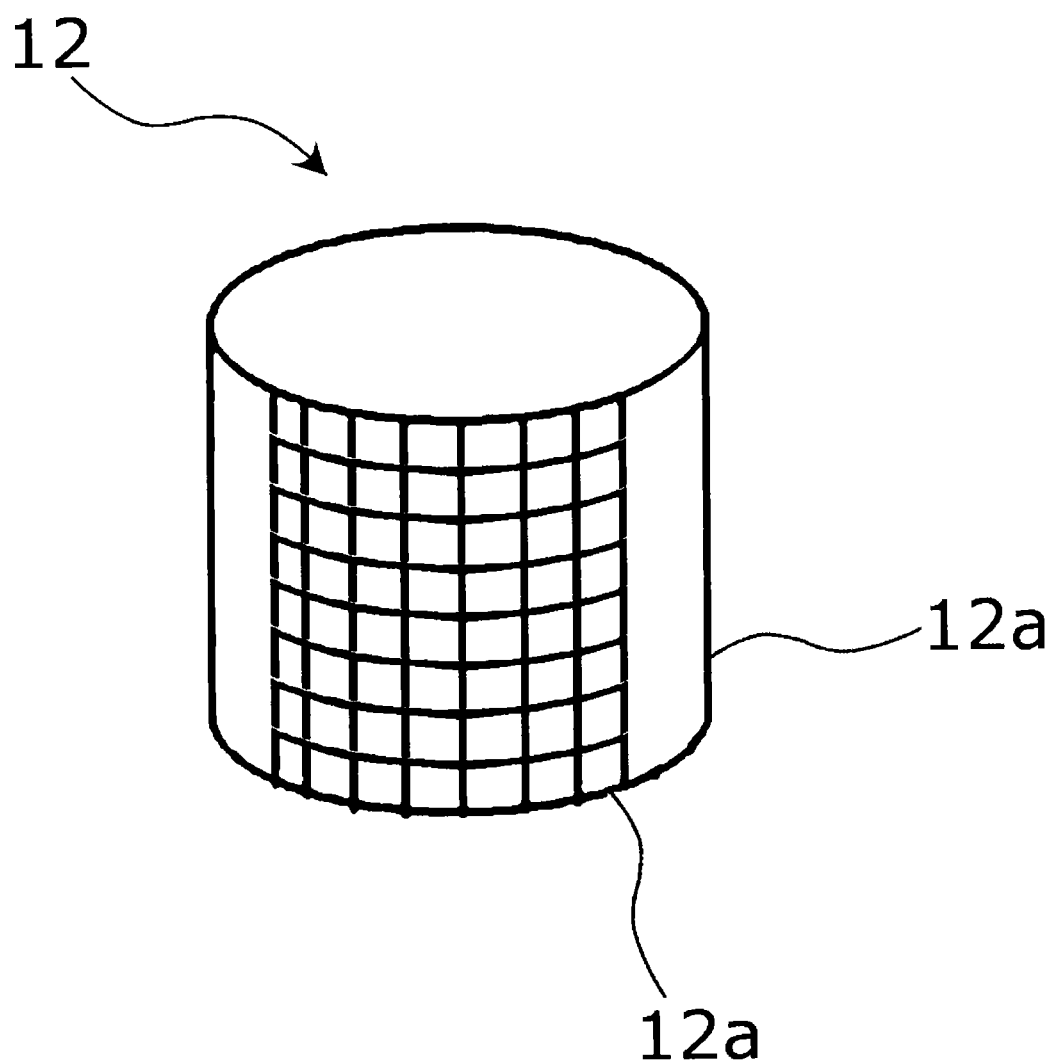
FIG. 3D is a schematic perspective view of the ultrasound transducer.

Referring to FIGS. 3B to 3D, other examples of the structure of the ultrasound transducer 12 are described. FIGS. 3B to 3D each illustrate a schematic perspective view of the ultrasound transducer 12. FIG. 3C illustrates the 1D array ultrasound transducer 12, while FIGS. 3B and 3D illustrate the 2D array ultrasound transducer 12. Besides, FIG. 3B illustrates the ultrasound transducer 12, in which the ultrasound oscillators 12a are provided all over the outer peripheral surface of the support. FIGS. 3C and 3D illustrate the ultrasound transducer 12, in which the ultrasound oscillators 12a are provided to a part of the outer peripheral surface of the support.

In the example of FIG. 3B, the ultrasound oscillators 12a are arranged in a 2D array all over the outer peripheral surface of the support. In this structure, the transmit-receive controller 14 (described later) is capable of switching the elements to be driven as well as deflecting and converging ultrasound waves (ultrasound beams) by electronic scanning. In the ultrasound transducer 12 illustrated in FIG. 3B, the transmit-receive controller 14 can deflect and converge ultrasound waves, by electronic scanning, not only in a direction in which the elements are arrayed (azimuth direction), but also in the elevation direction substantially perpendicular to the direction. Accordingly, there may be no need to rotate and tilt the ultrasound transducer 12. In this case, the structure does not include the direction controller 16 and the drive unit 18. The acoustic lens 12c may also not be included.

In the example of FIG. 3C, the ultrasound oscillators 12a are arranged in a 1D array in a part in the circumferential direction of the outer peripheral surface of the support. That is, for example, when the support is of a cylindrical form, the ultrasound oscillators 12a are arrayed in an area within a predetermined angle range (e.g., 60°) from the central axis in the outer peripheral surface. In this structure, upon receipt of an instruction signal from the main body 101, the direction controller 16 and the drive unit 18 (described later) perform rotating or tilting of the ultrasound transducer 12, or both.

In the example of FIG. 3D, the ultrasound oscillators 12a are arranged in a 2D array in a part in the circumferential direction of the outer peripheral surface of the support. In this structure, upon receipt of an instruction signal from the main body 101, the direction controller 16 and the drive unit 18 (described later) rotate the ultrasound transducer 12. The condition where the ultrasound oscillators 12a are arrayed in a part means that, for example, when the support is of a cylindrical form, the ultrasound oscillators 12a are arrayed in the azimuth and elevation directions in an area within a predetermined angle range (e.g., 60°) from the central axis in the outer peripheral surface.

(Modification of End Part)

If the used as the piezoelectric element is among those having low acoustic impedance such as PVDF, the backing layer may be configured to reflect ultrasound waves radiated thereto instead of absorbing them. For example, a material that doubles as the backing layer and the support of the ultrasound oscillators 12a may be used. The use of a shape-memory alloy as the material enables the end part 10 having the following structure. The modification of the end part 10 is described below with reference to FIG. 2D.

Figure 2D:
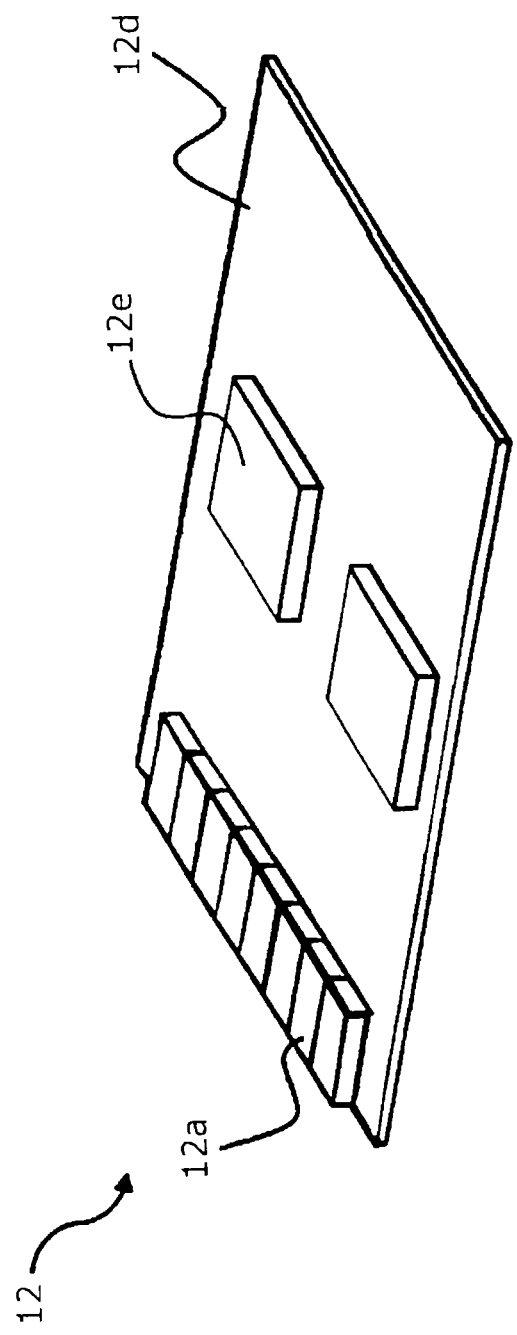
FIG. 2D is a schematic perspective view of a flexible printed circuit board.

The container 10a is configured such that the entire end part 10 is contracted when inserted into the subject's body. As illustrated in FIG. 2D, layers from the acoustic matching layer to the piezoelectric element are arranged on a flexible printed circuit (FPC) board 12d. On the FPC board 12d may be arranged an integrated circuit (IC) 12e having the function of the transmit-receive controller 14 and the like. The transmit-receive controller 14 is electrically connected to the electrode of the piezoelectric element via a pattern formed on the FPC board 12d and the like. The FPC board 12d is formed on the backing layer made of a shape-memory alloy.

The container 10a is configured such that, having been inserted in the subject's body, for example, when placed in the esophagus, the entire end part 10 is expanded by the injection of liquid such as water and the like through the cable 11 (see FIG. 2B). When the container 10a is expanded, a predetermined space is formed therein. The shape-memory alloy as the backing layer is configured to recover, for example, cylindrical or columnar form as illustrated in FIG. 3A, when being expanded. By the discharge (suction, etc.) of liquid injected in the container 10a, the entire end part 10 is contracted.

The ultrasound transducer 12 is supported by the FPC board 12d and the backing layer made of a shape-memory alloy. Accordingly, in response to the contraction of the container 10a, the entire ultrasound transducer 12 is also contracted. With this structure, the end part 10 becomes smaller when being contracted. Thus, the operator can arbitrarily expand/contract the end part 10, and thereby can easily insert and remove the end part 10 into/from the subject's body.

(Transmit-Receive Controller)

Figure 4:
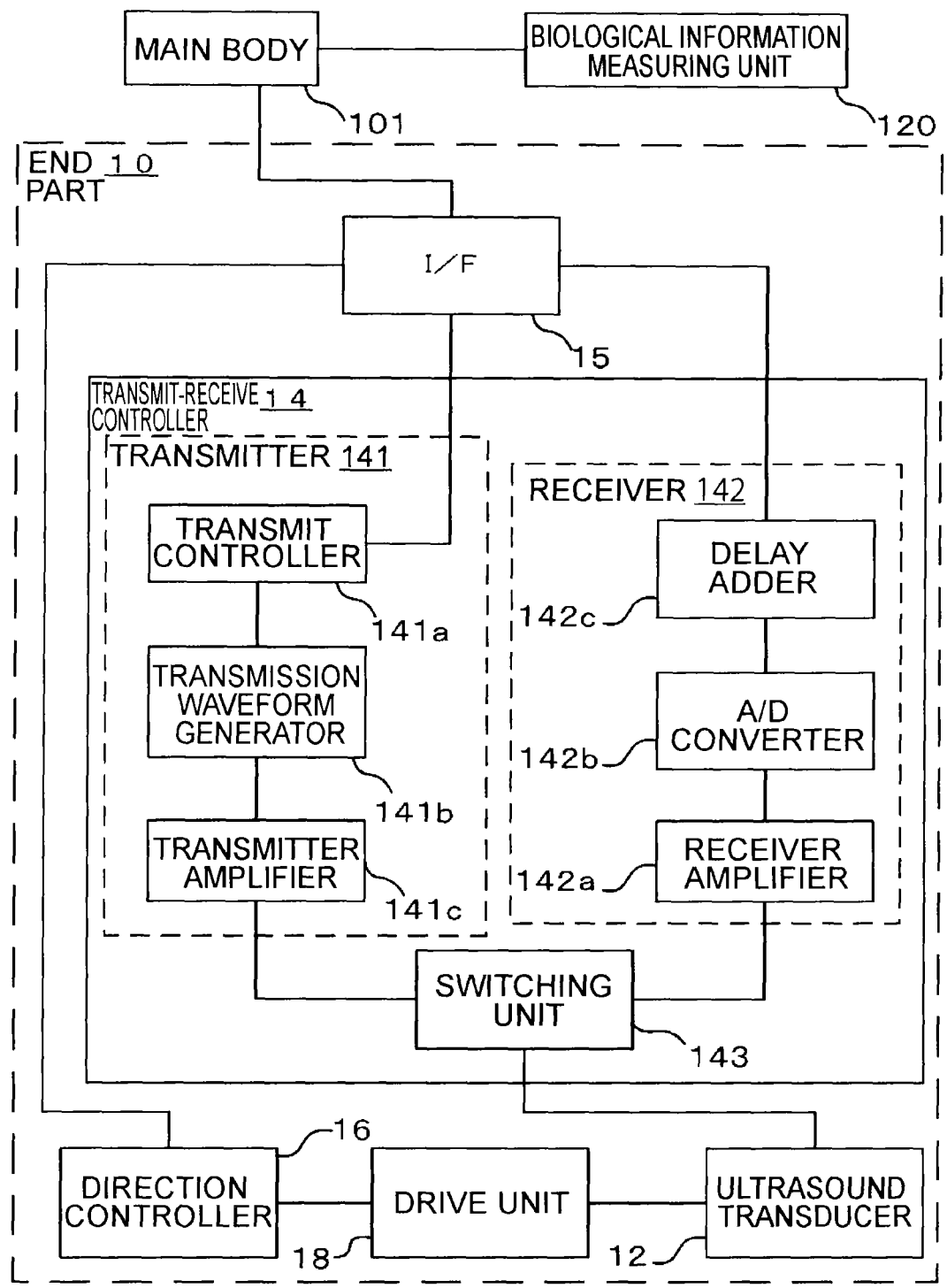
FIG. 4 is a schematic block diagram illustrating an example of the functional structure of an end part of an ultrasound diagnosis apparatus according to a first embodiment.

Next, referring to FIG. 4, a description is given of the transmit-receive controller 14 of the end part 10. FIG. 4 is a schematic block diagram illustrating an example of the functional structure of the end part 10 of the ultrasound diagnosis apparatus 100 of the first embodiment. As illustrated in FIG. 4, the transmit-receive controller 14 includes a transmitter 141, a receiver 142, and a switching unit 143. They are each described below.

(Transmitter)

The transmitter 141 of the end part 10 includes a transmit controller 141a, a transmission waveform generator 141b, and a transmitter amplifier 141c. The transmitter 141 receives an instruction signal on the transmission of ultrasound waves from the main body 101 (a transmitter/receiver unit 105 or the like, see FIG. 5) through the I/F 15. The transmitter 141 further includes a clock generation circuit, a transmitter delay circuit, and the like (not illustrated) controlled by the transmit controller 141a. The clock generation circuit generates clock signals for determining the transmission frequency and the transmission timing of ultrasound waves. For example, the clock generation circuit feeds the transmitter delay circuit with a reference clock signal. The transmitter delay circuit sends the transmission waveform generator 141b a drive signal having a predetermined delay time. The predetermined delay time is determined based on the transmission focal point of ultrasound waves.

The transmission waveform generator 141b includes, for example, a pulser circuit (not illustrated). The pulser circuit includes therein as many pulsers as individual channels corresponding to the ultrasound oscillators 12a, and generates transmission drive pulses. The pulser circuit repeatedly generates a rate pulse at a predetermined pulse repetition frequency (PRF). The rate pulses are distributed into the number of the channels, and sent to the transmitter delay circuit.

The transmitter delay circuit of the transmit controller 141a provides the rate pulse with a transmission delay time related to the transmission direction and the transmission focus. Transmission drive pulses are generated at timing based on the rate pulses each being delayed. The transmission drive pulses are amplified by the transmitter amplifier 141c, and sent to the switching unit 143. As described above, the transmitter delay circuit provides the pulser circuit with a delay time to focus ultrasound waves for transmission to converge ultrasound waves into a beam. With this, the transmission directivity of the ultrasound waves is determined. In addition, the transmitter delay circuit changes the transmission delay time to be given to each rate pulse, thereby controlling the transmission direction of ultrasound waves from the ultrasound wavefronts of the ultrasound oscillators 12a.

(Switching Unit)

The switching unit 143 has a switch relating to transmitting/receiving of ultrasound waves, and controls switching between the transmitter 141 and the receiver 142. If scan mode on the main body 101 side is set to continuous wave Doppler (CWD) mode, as described below, the switching unit 143 connects some elements of the ultrasound oscillators 12a to the transmitter 141 for transmission, and connects some others to the receiver 142 for reception.

If the scan mode on the main body 101 side is set to perform B (brightness) mode and pulsed wave Doppler (PWD) mode in parallel, the switching unit 143 alternately repeats control to sequentially switch elements to be driven according to the B mode and control to switch to elements that transmit ultrasound waves toward a set sample volume (sampling gate). In the B mode, a group of elements to be driven are shifted in the element array direction to control the transmission direction of ultrasound waves or the like.

Besides, the switching unit 143 switches sub-arrays each including a group of elements in m rows×n columns (a group of oscillators) in the 2D array ultrasound transducer 12. A transmission drive pulse from the transmitter amplifier 141c is applied to each element of the sub-array connected to the switch of the switching unit 143, and the piezoelectric element is driven.

(Receiver)

The receiver 142 of the end part 10 receives echo signals corresponding to ultrasound waves reflected from the subject. The receiver 142 amplifies the echo signals received by the ultrasound transducer 12, and also adds delay thereto. By the delay addition of the receiver 142, the analog echo signals are converted to digital data having been subjected to phasing (i.e., subjected to beam forming). Specific examples are as follows. The receiver 142 includes a receiver amplifier 142a, an A/D converter 142b, and a delay adder 142c. The receiver 142 may further include a sub-array delay adder (not illustrated). The receiver amplifier 142a amplifies echo signals received from the ultrasound transducer 12 with respect to each receiver channel. The A/D converter 142b converts the amplified echo signals to digital signals. Having been converted into digital signals, the echo signals are each stored in a digital memory (not illustrated). The digital memory is provided for each channel (or each element). Each echo signal is stored in the corresponding digital memory. The echo signal is also stored in an address corresponding to the time it is received. The A/D converter 142b is capable of thinning out data that has been filtered according to the bandwidth of the echo signal. If the receiver 142 has the sub-array delay adder (not illustrated), the sub-array delay adder can add echo signals from adjacent elements in the ultrasound oscillators 12a.

The delay adder 142c provides the echo signals each converted into a digital signal with a delay time required to determine the reception directivity. The reception delay time is calculated for each element. The delay adder 142c adds up the echo signals having the delay time. The delay adder 142c reads each of the echo signals from the digital memory as appropriate based on the required delay time calculated, and adds up them. The delay adder 142c repeats this addition while changing a reception focus position along the transmission beam. The addition emphasizes a reflection component from a direction corresponding to the reception directivity. The received beam signal processed by the receiver 142 is sent to a signal processor (a B-mode signal processing unit, a Doppler signal processing unit) via the I/F 15, the transmitter/receiver unit 105, or the like.

(Direction Controller, Drive Unit)

In response to an instruction signal on the transmission direction of ultrasound waves from the main body 101, the direction controller 16 controls the drive unit 18. For example, the direction controller 16 drives the drive unit 18 to change the angle or orientation of the wavefront of the ultrasound waves according to ROI (Region of Interest) set on the main body 101 side. The drive unit 18 is comprised of, for example, a micro-actuator such as an ultrasound motor. The drive unit 18 is driven under the control of the direction controller 16. The drive unit 18 is connected to the ultrasound transducer 12. With this structure, when the drive unit 18 is driven, the ultrasound transducer 12 is rotated or tilted. Thus, by driving the drive unit 18, the transmission direction of ultrasound waves can be changed in the ultrasound transducer 12.

<Structure of Biological Information Measuring Unit>

In FIG. 5, the biological information measuring unit 120 is connected to the main body 101. The biological information measuring unit 120 generates information indicating the conditions of the subject such as a biological signal, and sends the generated information to the main body 101. Examples of the biological information measuring unit 120 include bioelectric equipment (electrocardiograph, electroencephalograph, electromyography, etc.), respiratory equipment (respiratory flow meters, electronic spirometers, respiratory resistance meters, etc.), and medical monitoring equipment (singular monitor (bedside monitor), multiple monitors (central monitor), etc.), and the like. The medical monitoring equipment is configured to monitor vital signs such as ECG, blood pressure, respiratory rate, body temperature, pulse rate, blood oxygen saturation, exhaled gas partial pressure, and the like. Although FIG. 5 illustrates the biological information measuring unit 120 that is located outside the main body 101, some part thereof may be arranged in the main body 101 so that the measurement is performed in the main body 101. Besides, the biological information measuring unit 120 may be configured to analyze biological information in real time depending on the settings, and send the analysis result to the main body 101.

<Structure of Main Body>

Next, the control and the operation of each part of the main body 101 are described with reference to FIG. 5. The ultrasound diagnosis apparatus 100 illustrated in FIG. 5 is, for example, used to obtain such images as those indicating the form of biological tissues such as the heart (see FIG. 6) and those indicating the state of blood flow (see FIG. 7A). As illustrated in FIG. 5, in the ultrasound diagnosis apparatus 100, the main body 101 is connected to the end part 10 and the biological information measuring unit 120. The end part 10 corresponds to an example of "ultrasound transmitter/receiver". FIG. 5 is a schematic block diagram illustrating an example of the functional structure of the main body 101 of the ultrasound diagnosis apparatus of the first embodiment.

The main body 101 includes therein units for performing input/output operations, calculations, controls, and the like of the ultrasound diagnosis apparatus 100 (see FIG. 5). In FIG. 5, the main body 101 includes, as the functional units, the operation unit 102, the display unit 103, a main control unit 104, the transmitter/receiver unit 105, the evaluation value acquisition unit 107, a signal processor 108, a generating unit 109, the determination unit 110, and the output unit 111. Incidentally, the biological information measuring unit 120 may be included in the configuration of the ultrasound diagnosis apparatus 100. The main body 101 may include a power supply connected to the end part 10 via the cable 11.

(Operation Unit)

In response to operation by the operator, the operation unit 102 feeds signals and information corresponding to the operation to each unit. Examples of the operation unit 102 are not limited to a keyboard and a pointing device such as a mouse, but include any other user interfaces. For example, the input function of the operation unit 102 may be implemented as a software keyboard (softkey) on the touch panel integrated with the display unit 103. The operation unit 102 may have a function of receiving input of signals and information via media and networks. Note that, in the following, the ultrasound image includes not only anatomical images such as B-mode images but also waveform images based on the motion information of tissues and blood flow and color display images of brightness and color based on the motion information of tissues and blood flow.

If, for example, the operator operates a FREEZE button or an end button on the operation unit 102, transmitting/receiving of ultrasound waves is terminated or paused. The operator can set a value as to the normal range for the determination process (described later) by the operation unit 102. The set information is stored in the storage unit (not illustrated). Using the operation unit 102, the operator can also select and set how to provide the result of the determination process (output method). The operator can determine the initial settings, such as scan mode for ultrasound waves and the like, through the operation unit 102. Further, the operator can specify sample volume (sampling gate) in Doppler mode through the operation unit 102. Further, the operator can determine the settings for monitoring biological information such as cardiac ejection fraction through the operation unit 102.

(Display Unit)

The display unit 103 displays ultrasound images as well as operation screens, setting screens, and the like. Examples of the display unit 103 include any display devices such as a cathode ray tube (CRT), a liquid crystal display (LCD), a plasma display panel, an organic electroluminescent display (OELD), a field emission display (FED), and the like.

(Main Control Unit)

The main control unit 104 includes CPU (Central Processing Unit), ROM (Read Only Memory), RAM (Random Access Memory), and the like. The CPU loads a control program into the RAM as appropriate, and thereby implementing the function of the main control unit 104. That is, the main control unit 104 controls each part in the main body 101 as follows. To measure a plurality of types of functions of tissues of the subject including a predetermined site, the main control unit 104 is capable of operating as a controller that switches at least one of the following: the transmission method of ultrasound waves by the end part 10, the type of images to be generated, and the evaluation method used by the evaluation value acquisition unit 107.

(Transmitter/Receiver Unit; Transmitter Unit)

The transmitter/receiver unit 105 of the main body 101 transmits a signal related to the driving of the ultrasound transducer 12 to the transmit-receive controller 14 of the end part 10 according to selected scan mode. For example, the main control unit 104 receives a selection operation of scan mode (scan sequence) through the operation unit 102. In response to this operation, the main control unit 104 controls the transmitter/receiver unit 105 depending on the selected scan mode. According to the selected scan mode, transmission frequency, transmission driving voltage, and the like are changed. As the scan mode, such modes as follows can be selected: B-mode, power Doppler mode (PDI; Power Doppler Imaging), pulsed Doppler mode, continuous wave Doppler mode, color Doppler mode (CDI; Color Doppler Imaging/CFM; Color Flow Mapping), tissue Doppler mode (TDI; Tissue Doppler imaging), M (motion) mode, and the like. In addition, any combination of them is also selectable for the scan mode.

In the pulsed Doppler mode, the direction of transmission beams and transmission focal point (range related to the depth direction and the position of an observation area) are set based on the sample volume (sampling gate). The sample volume is, for example, set by the operator specifying any range on a displayed B-mode image BI (FIG. 6) using the operation unit 102. In the continuous wave Doppler mode, a region of space occupied by transmission beams is the observation area.

When capturing images in predetermined cardiac time phase, the main control unit 104 receives ECG waveform from the biological information measuring unit 120, and extracts the predetermined cardiac time phase. Correspondingly to the extracted cardiac time phase, the main control unit 104 sends a trigger signal to the transmitter/receiver unit 105. At the start of monitoring, regardless of whether a trigger signal has been received from the main control unit 104, ultrasound waves may be transmitted for the predetermined number of heartbeats.

(Transmitter/Receiver Unit; Receiver Unit)

From the end part 10, the receiver unit of the transmitter/receiver unit 105 of the main body 101 receives a digital echo signal having been subjected to predetermined processing by the transmitter 141. The echo signal is sent to the signal processor 108.

(Signal Processor; B-Mode Signal Processing Unit)

The signal processor 108 includes a B-mode signal processing unit and a Doppler signal processing unit. Having received the received signal from the receiver unit of the transmitter/receiver unit 105, the B-mode signal processing unit creates a visual image of amplitude information of the signal. Specifically, the B-mode signal processing unit performs band-pass filtering on the received beam signal, thereafter, detects the envelope of the output signal, and then compresses detected data by logarithmic transformation. Thus, the B-mode signal processing unit generates RAW data of a B-mode image.

(Signal Processor; Doppler Signal Processing Unit)

As Doppler processing, the Doppler signal processing unit removes Doppler shift frequency component by phase detection of the received beam signals, and performs fast Fourier transform (FFT). The Doppler signal processing unit extracts a Doppler shift by the frequency analysis of the received beam signal (Doppler signal). The Doppler signal processing unit extracts, based on the Doppler shift, contrast medium echo component as well as blood flow and tissues caused by Doppler effect, and generates RAW data of a Doppler image extracting mobile object information such as average velocity, variance, and power with respect to a plurality of points.

The Doppler signal processing unit may be configured to perform color Doppler processing. The blood flow information is visualized by the color Doppler processing. The blood flow information includes such information as velocity, distribution, and power. For example, the Doppler signal processing unit processes the received beam signal, thereby generating RAW data of a color flow mapping (CFM) image in the region of interest. In particular, the Doppler signal processing unit performs quadrature detection of the beam signal received from the transmitter/receiver unit 105. The Doppler signal processing unit then performs frequency analysis on the echo signal after the quadrature detection by autocorrelation method. By the frequency analysis, the Doppler signal processing unit calculates the variance and the average velocity of blood flow at each point of the sample. The Doppler signal processing unit generates the RAW data of the color flow mapping image representing the calculated variance and the average flow velocity by color. The Doppler signal processing unit also calculates the power of blood flow based on the received beam signal subjected to the quadrature detection. The Doppler signal processing unit generates the RAW data of the color flow mapping image representing the calculated power by color.

The signal processing units send the RAW data (ultrasound raster data) subjected to the signal processing to the generating unit 109. Incidentally, the B-mode signal processing unit and the Doppler signal processing unit of the embodiment can process both two-dimensional echo data and three-dimensional echo data.

(Generating Unit)

Figure 6:
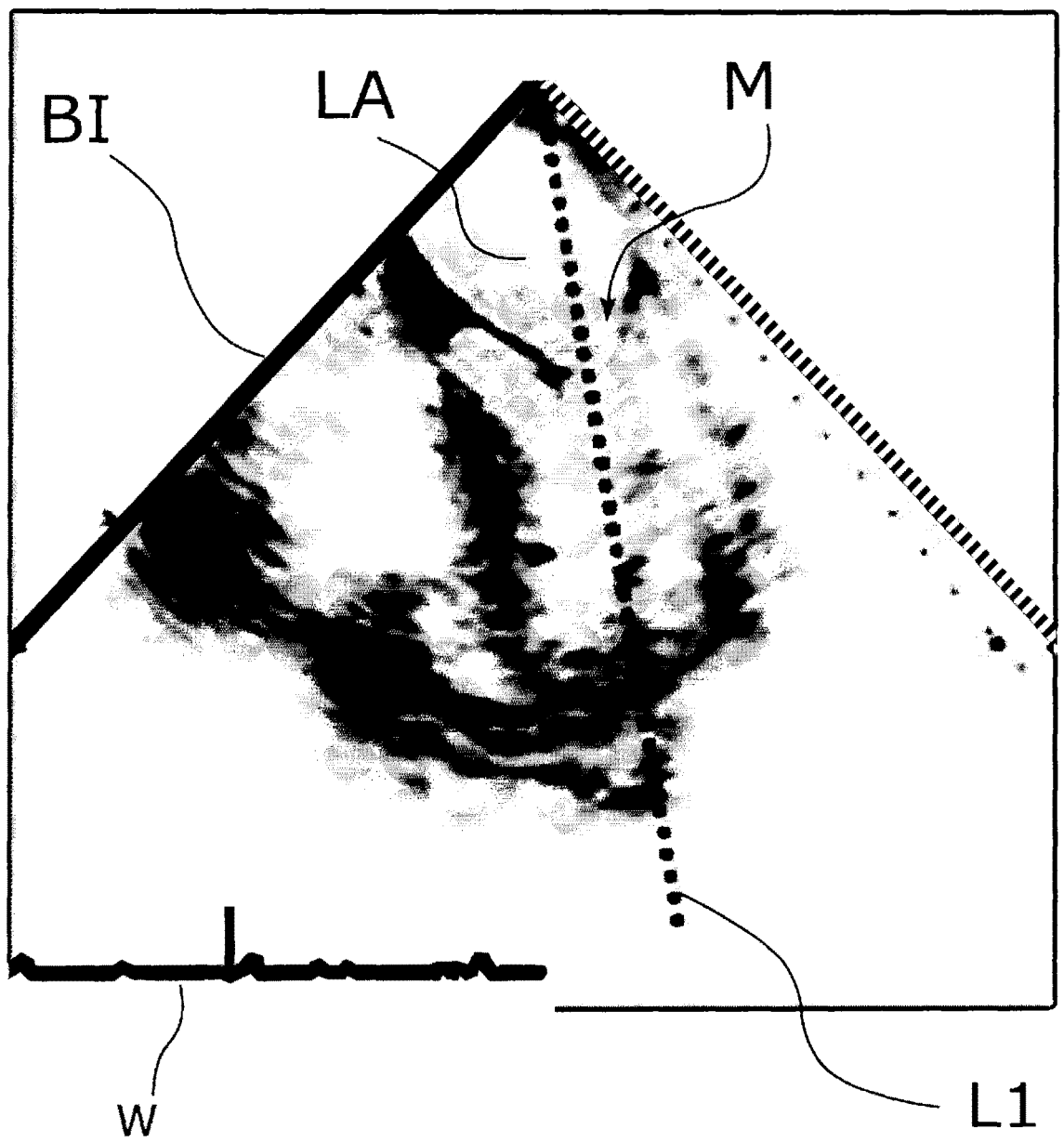
FIG. 6 is a schematic diagram of an example of a B-mode image generated by a generating unit of the first embodiment.
Figure 8:
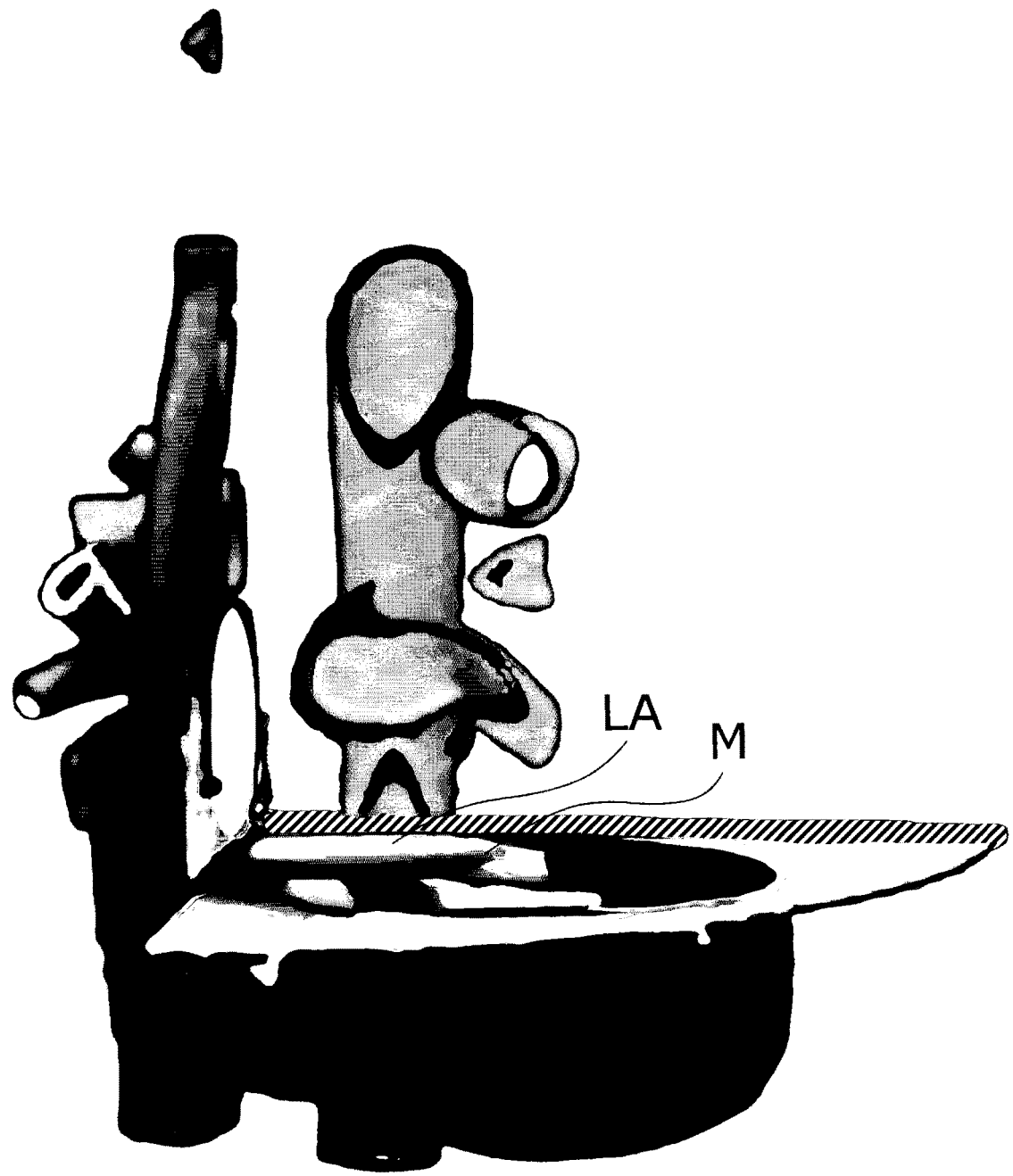
FIG. 8 is a schematic diagram illustrating a positional relationship for obtaining the B-mode image illustrated in FIG. 6.

With reference to FIGS. 6, 7A, 7B, and 8, the operation of the generating unit 109 is described. FIG. 6 is a schematic diagram of an example of a B-mode image BI generated by the generating unit 109 of the first embodiment. FIG. 7A is a schematic diagram of an example of a Doppler spectrum image generated by the generating unit 109. FIG. 7B is a schematic diagram of an example of the Doppler spectrum image illustrated in FIG. 7A displayed in parallel with ECG (electrocardiogram) waveform fed by the biological information measuring unit 120. FIG. 8 is a schematic diagram of screen data illustrating a positional relationship for obtaining the cross section of the B-mode image BI illustrated in FIG. 6. Having received RAW data based on echo signals for the predetermined number of heartbeats, the generating unit 109 generates ultrasound image data corresponding to the number of heartbeats.

The generating unit 109 generates ultrasound image data based on the RAW data after the signal processing output from the signal processor (the B-mode signal processing unit, the Doppler signal processing unit). The generating unit 109 includes, for example, DSC (Digital Scan Converter). The generating unit 109 converts the RAW data subjected to the signal processing represented by a signal sequence of a scan line into image data represented by a Cartesian coordinate system (scan conversion). For example, by applying the scan conversion to the RAW data subjected to the signal processing by the B-mode signal processing unit, the generating unit 109 generates B-mode image data representing signal strength by brightness for each form of the tissues of the subject (see FIG. 6). As illustrated, FIG. 6 is a four-chamber cross-sectional view, approached from the esophagus (see FIG. 8). FIG. 6 illustrates left atrium LA, mitral valve M, and a broken line L1 indicating the transmission direction of ultrasound waves.

Besides, the generating unit 109 performs coordinate transformation on the RAW data having undergone the color Doppler processing or the Doppler processing, and generates data of the Doppler image and data of the color flow mapping image that can be displayed on the display unit 103. For example, based on the result of the frequency analysis of the Doppler signal (echo signal) using FFT (Fast Fourier Transform) by the Doppler signal processing unit, the generating unit 109 generates a Doppler spectrum image where the velocity information of the mobile object (velocity information of blood flow, tissues, etc.) is drawn along the time series (see FIG. 7A).

In FIG. 7A, the vertical axis indicates frequency f (velocity v), while the horizontal axis indicates time t, and thus the spectrum is represented (FFT display). Additionally, in the waveform display, the crest value represents the magnitude of the velocity, and the brightness represents the strength of the Doppler spectrum (corresponding to the power of the Doppler signal). In FIG. 7A, the tone is displayed in reverse to enhance the viewability of the image (the same is applied to FIG. 7B).

After ultrasound waves are transmitted/received with time through the end part 10, Doppler spectrum images are sequentially generated by the generating unit 109 through the above processing. The display unit 103 sequentially displays the generated images, and thus the state that the frequency f (the velocity v of the object) changes from moment to moment is displayed as a pattern.

The generating unit 109 can obtain ECG waveform from the biological information measuring unit 120 connected to the main body 101 via the main control unit 104 and the transmitter/receiver unit 105. As illustrated in FIG. 7B, based on the ECG waveform obtained, the generating unit 109 generates an image capable of representing the Doppler spectrum image and the ECG waveform synchronously in parallel.

Also, for example, from the RAW data of a color flow mapping image, the generating unit 109 generates color flow mapping images as an average velocity image indicating mobile object information (blood flow information, tissue motion information, etc.) a variance image, a power image, and a combination of these. The generating unit 109 may generate a composite image by combining any images from the B-mode image BI, the color flow mapping image, and the Doppler image. For example, the generating unit 109 generates a color flow mapping image by superimposing a color display based on the blood flow information on the B-mode image BI (or MPR image) as well as generating a Doppler spectrum image by pulsed Doppler mode. Further, the generating unit 109 can generate an image capable of representing the color flow mapping image and the Doppler spectrum image in parallel with the ECG waveform based on the ECG waveform obtained from the biological information measuring unit 120.

When a volume data processing unit (not illustrated) is provided to the signal processor of the main body 101, the generating unit 109 may also display a volume rendering image and an MPR image. In this case, based on the echo signal received by the ultrasound transducer 12, the signal processor generates volume data representing the three-dimensional shape of tissues in the subject's body directly from the RAW data, or from image data generated by the digital scan converter. Further, having obtained volume data from the signal processor, the generating unit 109 generates a volume rendering image. The generating unit 109 can also generate an MPR image from the volume data. FIG. 8 illustrated a four-chamber cross section.

(Direction Setting Unit)

The direction setting unit (not illustrated) sets the transmission direction of ultrasound waves by the ultrasound transducer 12 in the end part 10. The transmission direction is set based on operator's operation on the operation unit 102. A direction setting unit 113 sends the transmit-receive controller 14 or the direction controller 16 of the end part 10 determined transmission direction data. The direction setting unit includes a storage unit (not illustrated) to store sample volume and the transmission direction data.

With respect to the setting of the transmission direction of ultrasound waves, the direction setting unit receives such operations as selecting scan mode, setting sample volume, rotating/tilting the ultrasound transducer 12, and the like. The direction setting unit also sets elements (or channels) to apply a drive signal in the ultrasound transducer 12 of the end part 10 depending on scan mode (continuous wave Doppler mode, etc.).

The information set for the transmission direction of ultrasound waves according to scan mode selection and sample volume setting (elements to be driven, angle/direction with respect to the ultrasound wavefront, etc.) is sent to the transmit-receive controller 14 of the end part 10 via the transmitter/receiver unit 105. The information set for the transmission direction of ultrasound waves according to the rotation/tilting of the ultrasound transducer 12 (the amount of rotation, the tilt angle of the ultrasound transducer 12, etc.) is sent to the direction controller 16 of the end part 10.

(Evaluation Value Acquisition Unit)

Described below is the operation of the evaluation value acquisition unit 107. The evaluation value acquisition unit 107 of this embodiment acquires evaluation values indicating the evaluation of the function of body tissue by an evaluation method set in advance from each of anatomical images acquired over time (a first anatomical image, and a second anatomical image acquired after the first anatomical image). The anatomical images acquired over time are an example of an anatomical image group. In the ultrasound diagnosis apparatus 100, the evaluation method is classified into anatomical evaluation and functional evaluation, and a plurality of types of methods are stored for each category. It is assumed herein that one of the evaluation methods is selected by selection operation through the operation unit 102.

After the ultrasound diagnosis apparatus 100 starts monitoring for ultrasound examination, having received an anatomical image (B-mode images, MPR images, etc.) or an M-mode image from the generating unit 109, the evaluation value acquisition unit 107 evaluates the anatomical image according to an evaluation method set in advance. That is, the evaluation value acquisition unit 107 retrieves the evaluation method selected by the operator in the initial setting from a storage unit (not illustrated). The evaluation value acquisition unit 107 may retrieve one or a plurality of types of evaluation methods.

The evaluation value acquisition unit 107 obtains numerical information (hereinafter, sometimes referred to as "evaluation value") for the obtained ultrasound images by a calculation method of the retrieved evaluation method. Examples of the evaluation value calculated by the evaluation value acquisition unit 107 include a reference evaluation value and a compared evaluation value.

<<Calculation of Reference Evaluation Value>>

The evaluation value acquisition unit 107 obtains a reference evaluation value used in abnormality determination process (described later) by the determination unit 110. This is the reference evaluation value in this embodiment. The reference evaluation value is obtained when the subject is in the normal condition. In one example, upon start of ultrasound examination monitoring, the ultrasound diagnosis apparatus 100 receives ECG waveform from the biological information measuring unit 120. The main control unit 104 analyzes the ECG waveform, and determines whether there is any abnormality. As an example of the abnormality may be cited the case where non-periodic waveform appears in the received ECG waveform. As another example of the abnormality may be cited the case where, as a result of pattern matching between the pattern of abnormal ECG waveform stored in advance and that of the received ECG waveform, waveform with high similarity to the pattern of abnormal ECG waveform is detected. The similarity is determined by cross-correlation operation or the like.

Whether the subject is in the normal conditions or not may be determined by generating an ultrasound image through imaging so that a viewer can make reference to the ultrasound image. For example, the viewer may refer to the ultrasound image displayed on the display unit 103, and provide input determining that the subject is in the normal condition using the operation unit 102. With this, it may be determined that the condition of the subject is normal at the time.

Having determined that the subject is in the normal condition, the main control unit 104 sends a control signal to the evaluation value acquisition unit 107 to obtain a reference evaluation value. Upon receipt of the control signal, the evaluation value acquisition unit 107 obtains a reference evaluation value from ultrasound images acquired over time according to an evaluation method set in advance. The evaluation value acquisition unit 107 stores the obtained reference evaluation value in the storage unit (not illustrated).

<<Calculation of Compared Evaluation Value>>

There is a compared evaluation value that is usually obtained after the evaluation reference value. The compared evaluation value is a value to be compared to the reference value in the abnormality determination process. Specifically, the compared evaluation value is a value that the evaluation value acquisition unit 107 obtains sequentially by the evaluation method for the ultrasound images acquired over time through the ultrasound examination monitoring. The determination unit 110 compares the compared evaluation value with the reference evaluation value, thereby performing the abnormality determination process.

Described below are specific examples of the evaluation method performed by the evaluation value acquisition unit 107.

(Measurement of Left Ventricular Volume; Evaluation Method Example 1)

Figure 9A:
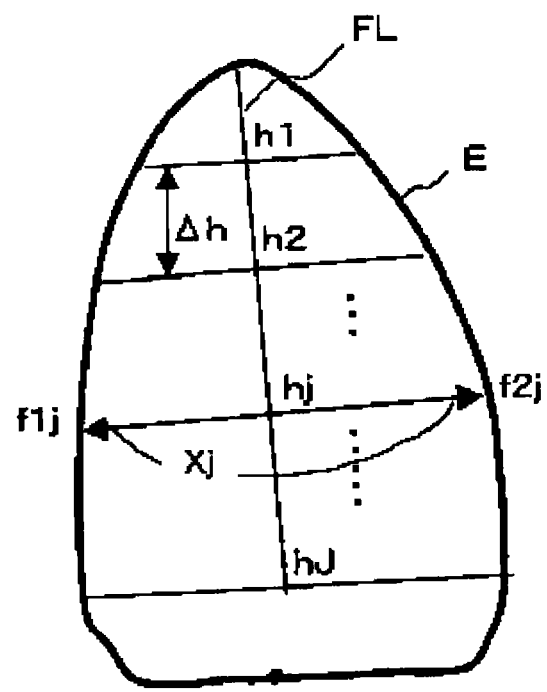
FIG. 9A is a schematic diagram illustrating an overview of a specific example of heart chamber volume measurement performed by an evaluation value acquisition unit.
Figure 9B:
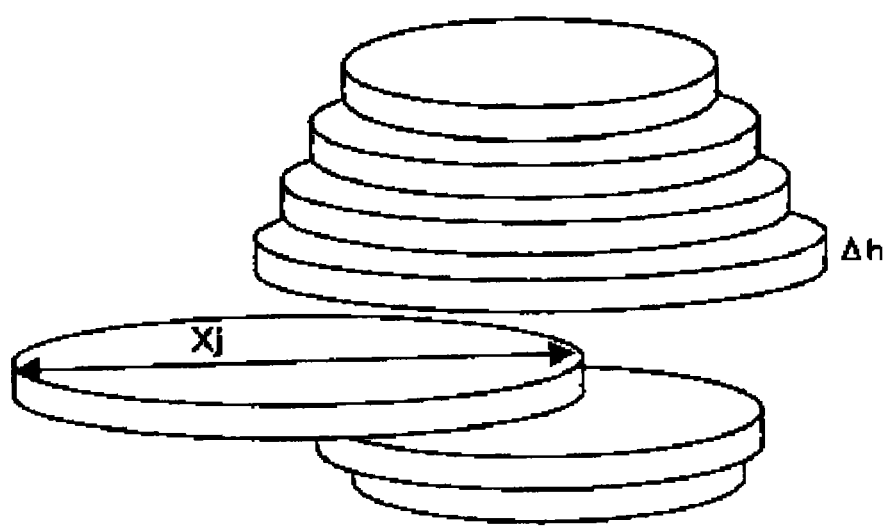
FIG. 9B is a schematic diagram illustrating an overview of a specific example of the heart chamber volume measurement performed by the evaluation value acquisition unit.

FIGS. 9A and 9B each illustrate a specific example of heart chamber volume measurement performed by the evaluation value acquisition unit 107. Having received selection operation through the operation unit 102, the evaluation value acquisition unit 107 selects M pieces of image data P1 to PM corresponding to desired time period T0 from time-series B-mode image data stored in the storage unit (not illustrated), and stores them separately. In addition, the evaluation value acquisition unit 107 detects a valve annulus from contour data generated for each of the image data P1 to PM, and sets the long axis FL of the heart based on the position of the valve annulus. Further, the evaluation value acquisition unit 107 draws a normal to the long axis FL from a dividing point hj (j=1 to J) obtained by dividing the long axis FL into J at interval Δh, and calculates length Xj (j=1 to J) between two intersections f1j and f2j where the normal crosses contour data E (see FIG. 9A).

Next, the evaluation value acquisition unit 107 approximates the volume by the sum of minute cylinders with height Δh set in advance and the length X1 to Xj obtained as above as diameter, i.e., using so-called Modified-Simpson method, thereby measuring the heart chamber volume in each time phase (see FIG. 9B). The heart chamber volume measured for each time phase is stored in a memory circuit (not illustrated) of the evaluation value acquisition unit 107 with the time phase as additional information.

(Measurement of Left Ventricular Volume; Evaluation Method Example 2)

Figure 10:
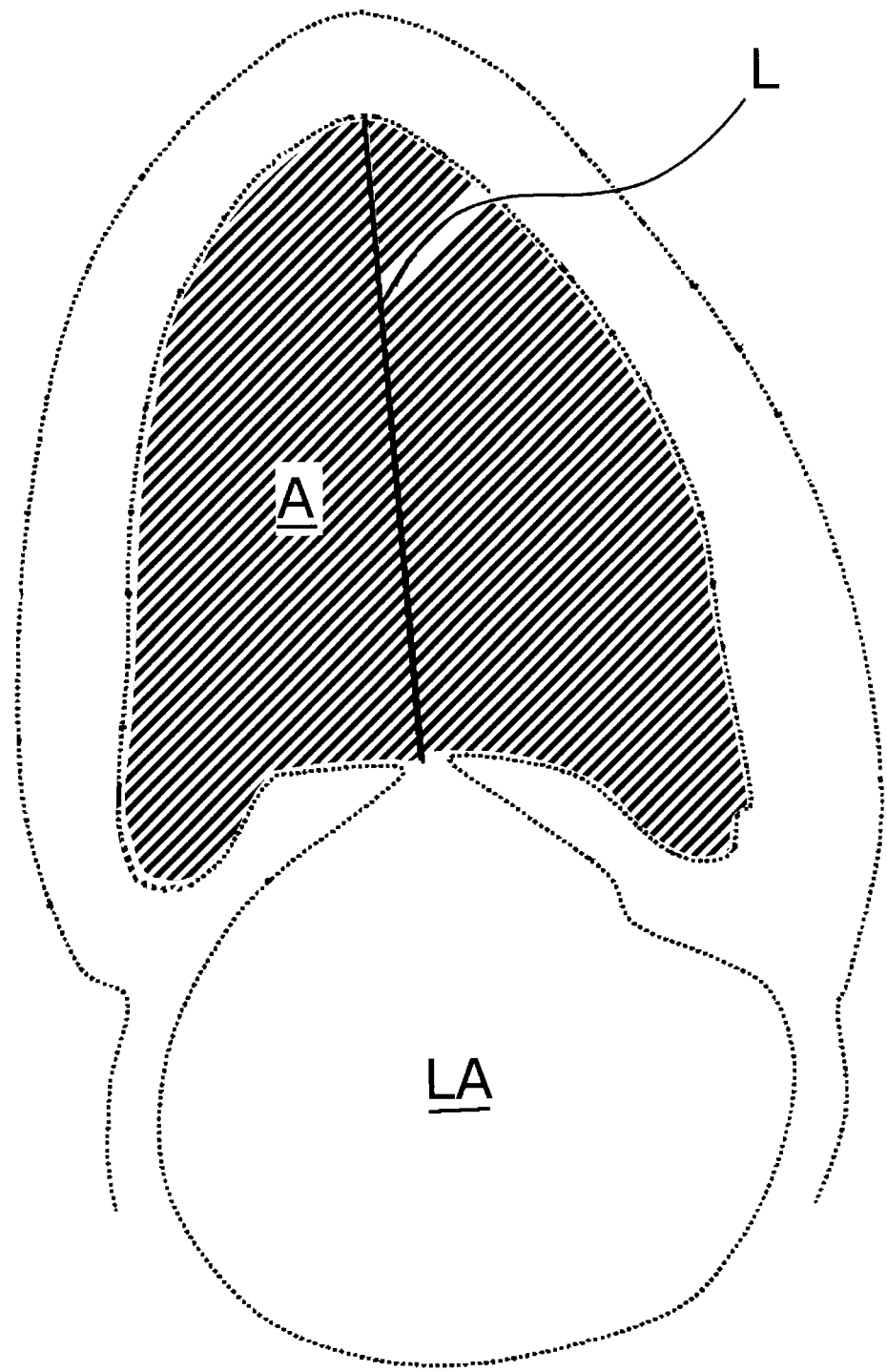
FIG. 10 is a schematic diagram of an apical two-chamber section.

With reference to FIG. 10, a description is given of another specific example of heart chamber volume measurement performed by the evaluation value acquisition unit 107. FIG. 10 is a schematic diagram of an apical two-chamber section. In this example, the evaluation value acquisition unit 107 obtains the left ventricular volume from a single 2D tomographic image. That is, the evaluation value acquisition unit 107 obtains the area of a single cross-section, and calculates the left ventricular volume based on this area (so-called single plane area-length method). On the assumption that the left ventricle is a spheroid, the evaluation value acquisition unit 107 measures the area of the cross-section of the left ventricle including the long axis of the left ventricle (A), and the length of the long axis of the left ventricle (L) as illustrated in FIG. 10. Besides, the evaluation value acquisition unit 107 uses the following formula (1):

$$D = \frac{4A}{\pi L} \quad (1)$$

and calculates the volume by the following formula (2):

$$V = \frac{\pi}{6} D^2 L \quad (2)$$

where D is the length of the short axis of the left ventricle.

That is, the evaluation value acquisition unit 107 calculates the volume using the following formula (3):

$$V = \left(\frac{\pi}{6}\right)\left(\frac{4A}{\pi L}\right)^2 L \quad (3)$$

The volume thus calculated is stored in the memory circuit (not illustrated) of the evaluation value acquisition unit 107 with the cardiac time phase.

(Measurement of Left Ventricular Volume; Evaluation Method Example 3)

Described below is still another specific example of heart chamber volume measurement performed by the evaluation value acquisition unit 107. In this example, the evaluation value acquisition unit 107 obtains the left ventricular volume from an M-mode image. This evaluation method is performed given that the M-mode image to be used is acquired in ultrasound transmission direction (beam direction) passing through the maximum minor axis of the left ventricle.

On the assumption that the left ventricle is a spheroid, the evaluation value acquisition unit 107 measures a straight-line distance from the endocardium surface of the left ventricular side of the interventricular septum to the endocardial surface of the posterior left ventricular wall on the parasternal long-axis or short-axis view. The evaluation value acquisition unit 107 performs the measurement at end-diastole and end-systole. The evaluation value acquisition unit 107 obtains the left ventricular end-diastolic dimension (LVDd) at end-diastole, and the left ventricular end-systolic dimension (LVDs) at end-systole, thereby calculating the volume. The Teichholz formula can be used for the calculation. The volume thus calculated is stored in the memory circuit (not illustrated) of the evaluation value acquisition unit 107.

(Determination Unit)

Described next is the operation of the determination unit 110. The determination unit 110 of the embodiment sequentially receives compared evaluation values obtained by the evaluation value acquisition unit 107. Having received a compared evaluation value, the determination unit 110 reads the reference evaluation value out of the storage unit (not illustrated). The determination unit 110 compares the compared evaluation value with the reference evaluation value. According to the evaluation method used by the evaluation value acquisition unit 107, the determination unit 110 reads information on the normal range of the evaluation value (hereinafter, sometimes referred to as "normal range") set in advance. The data to be read may be data of a threshold for the evaluation value.

The determination unit 110 determines whether the comparison result is within the normal range. The comparison result is numerical information on the ratio or the difference between the compared evaluation value and the reference evaluation value. When the compared evaluation value is within the normal range, the determination unit 110 determines that the value is normal. On the other hand, if the compared evaluation value is outside the normal range, the determination unit 110 determines that the value is abnormal. Having determined the compared evaluation value as being abnormal, the determination unit 110 sends a determination result indicating the abnormality to the display unit 103. The display unit 103 displays the determination result indicating the abnormality as a warning (e.g., "abnormality in the determination result of the evaluation value").

The determination unit 110 does not necessarily operate as above when determining the compared evaluation value as being abnormal. Having determined that the compared evaluation value is abnormal, the determination unit 110 may send a trigger signal to the output unit 111. The determination unit 110 may also send the output unit 111 the deviation amount between the compared evaluation value and the reference evaluation value. Here, the deviation amount refers to information on the ratio or the difference between the compared evaluation value and the reference evaluation value, or evaluation information evaluating the degree of deviation based on the information, and the like.

(Output Unit)

Upon receipt of the trigger signal from the determination unit 110, the output unit 111 notifies a warning by a method set in advance. For example, if capable of outputting sound, the output unit 111 may output warning sound. The warning sound as described herein includes alarm sound and a warning message in a predetermined language. As a warning message, the output unit 111 may output a voice message corresponding to the evaluation method (e.g., the evaluation of left ventricular systolic function) such as "decline in XX function", disease name (heart failure, etc.) corresponding to the determination result of the evaluation.

For another example of the warning process, the output unit 111 may be configured to output information to provide the warning as described above to a portable terminal or a terminal in the same medical institution. That is, in this configuration, the main body 101 can exchange information with an external terminal device via an interface (not illustrated). Examples of the external terminal device include PC connected to the main body 101 via LAN, mobile terminal devices having data communication function such as PHS, and the like.

Having received the determination result indicating the abnormality from the determination unit 110, the output unit 111 transmits the information related to the warning to the external terminal device. The external terminal device outputs warning sound based on the information related to the warning. The external terminal device may also display a warning message or the like on the display unit thereof.

<Operation>

Figure 11:
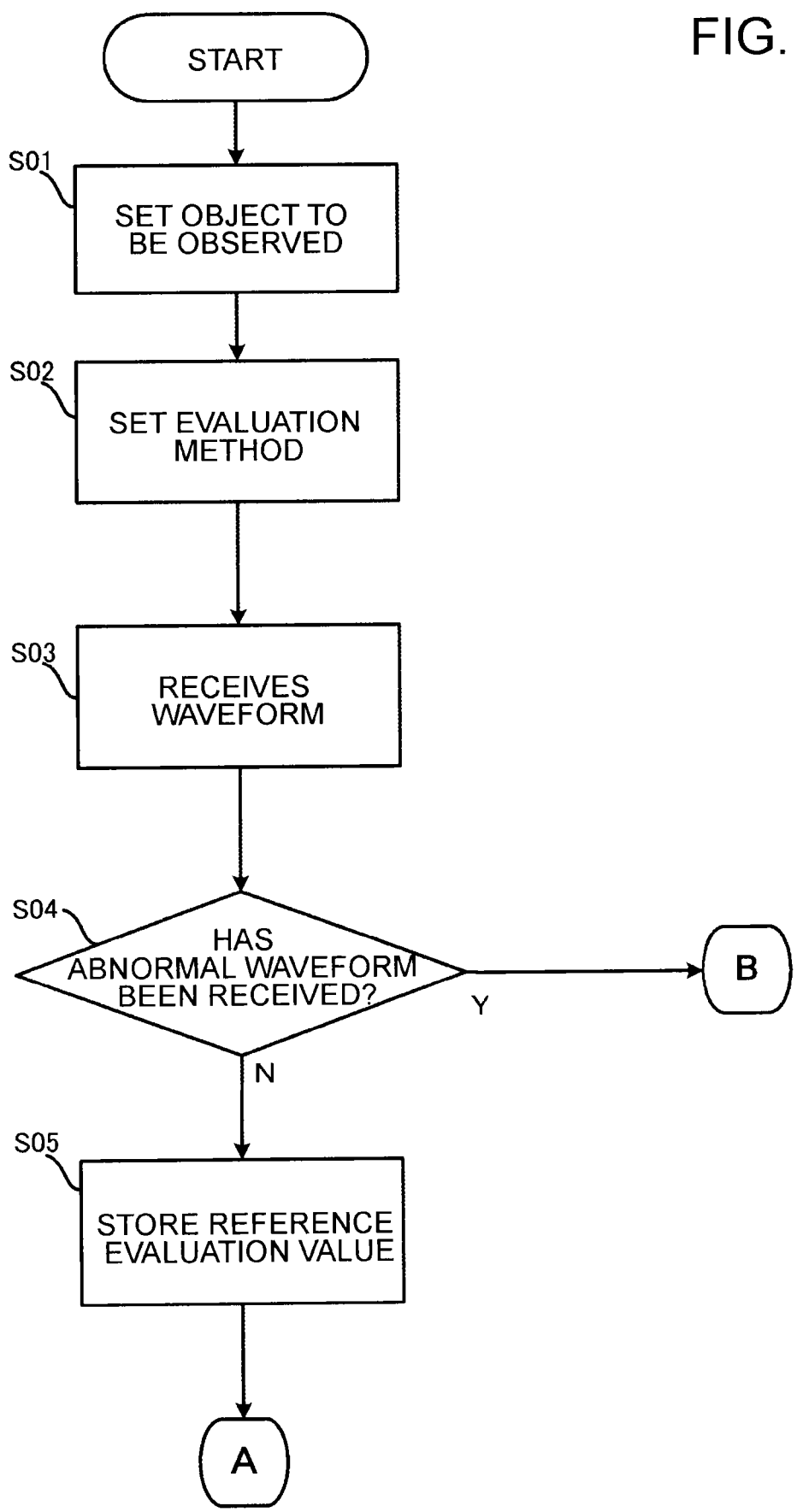
FIG. 11 is a flowchart schematically illustrating the operation of the ultrasound diagnosis apparatus of the first embodiment.
Figure 12:
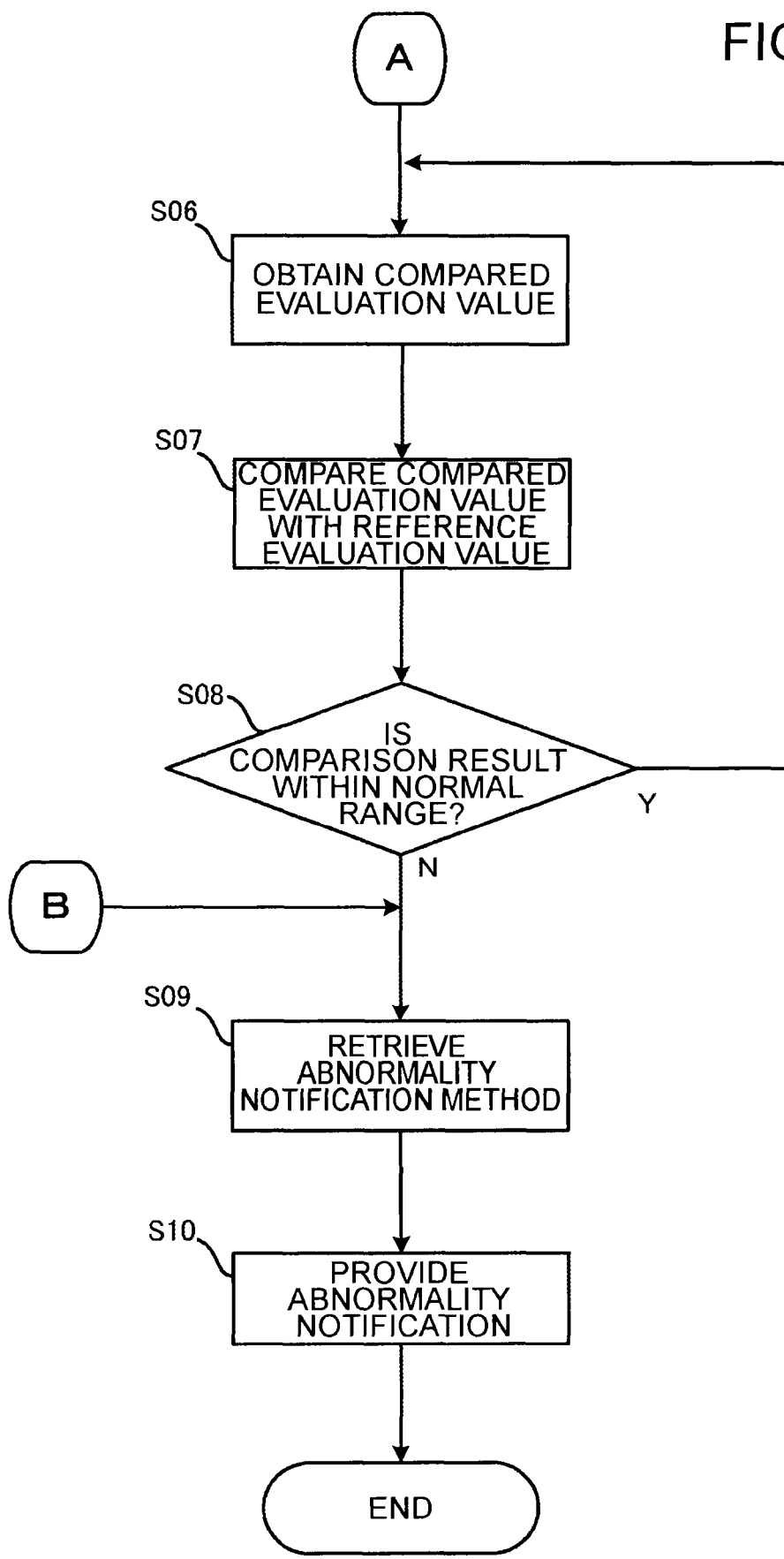
FIG. 12 is a flowchart schematically illustrating the operation of the ultrasound diagnosis apparatus of the first embodiment.

In the following, a description is given of a control flow to perform the intermittent imaging according to the embodiment with reference to FIGS. 11 and 12. FIGS. 11 and 12 are flowcharts schematically illustrating the operation of the ultrasound diagnosis apparatus 100 of the first embodiment.

(Step S01)

As an item in the initial setting, the operator sets the object of functional evaluation in the body tissues of the subject, i.e., an object to be observed by monitoring. The observation object set by the operator is stored in the storage unit (not illustrated).

(Step S02)

In addition, as another item in the initial setting, the operator sets the method of functional evaluation in the body tissues of the subject. For example, the main control unit 104 may be configured to display a setting screen (not illustrated) on the display unit 103 for setting of the evaluation method. In this example, the operator selects any one of evaluation methods from a drop-down list on the setting screen using the operation unit 102 to set the evaluation method. Based on the information of the observation object set in step S01, the main control unit 104 may display only evaluation methods corresponding to the observation object in a list. The evaluation method set by the operator is stored in the storage unit (not illustrated).

(Step S03)

The main control unit 104 receives a waveform based on a biological signal of the subject from the biological information measuring unit 120. At this point, transmitting/receiving of ultrasound waves may be started, and the generating unit 109 may start generating ultrasound images. When an ultrasound image is generated, the evaluation value acquisition unit 107 retrieves information on the evaluation method set in step S02, and calculates the evaluation value of the ultrasound image according to the evaluation method. This step is performed by after the determination as to abnormality in the conditions of the subject by the main control unit 104 (S04) at the latest.

(Step S04)

The main control unit 104 analyses the waveform. From the result of the analysis, the main control unit 104 determines whether a non-periodic waveform is detected. The main control unit 104 may determine whether a waveform with high similarity to an abnormal waveform pattern is detected.

(Step S05)

As a result of the determination in step S04, if an abnormal waveform is not detected (step S04; No), the evaluation value acquisition unit 107 stores the obtained evaluation value in the storage unit (not illustrated) as a reference evaluation value.

(Step S06)

After storing the reference evaluation value, the evaluation value acquisition unit 107 acquires an ultrasound image generated by the generating unit 109, and obtains a compared evaluation value according to the set evaluation method. The generating unit 109 sequentially generates ultrasound images over time. Accordingly, the evaluation value acquisition unit 107 sequentially obtains compared evaluation values. Having obtained the compared evaluation values, the evaluation value acquisition unit 107 sends them to the determination unit 110.

(Step S07)

In response to the compared evaluation value received from the evaluation value acquisition unit 107, the determination unit 110 reads the reference evaluation value out of the storage unit. In addition, the determination unit 110 reads, from the storage unit, information on the normal range according to the evaluation method used for the compared evaluation value. The determination unit 110 compares the compared evaluation value with the reference evaluation value. Since the compared evaluation values are calculated over time and sequentially sent from the evaluation value acquisition unit 107, the determination unit 110 repeats this comparison.

(Step S08)

The determination unit 110 determines whether the comparison result between the compared evaluation value and the reference evaluation value is within the normal range. As a result of the determination in step S08, when the comparison result is within the normal range (step S08; Yes), the determination unit 110 repeats steps S06 to S08.

(Step S09)

If an abnormal waveform is detected from the result of the determination in step S04 (step S04; Yes), the determination unit 110 reads, from the storage unit, an abnormality notification method according to the degree of the comparison result and the evaluation method without steps S05 to S08. The determination unit 110 retrieves an abnormality notification method according to the type of the abnormal waveform. This abnormality notification is performed in response to the detection of an abnormal waveform. Thus, it is different from the abnormality notification based on the determination result of the evaluation value. For example, the determination unit 110 retrieves an abnormality notification method of reporting disease name (or decline in the function of tissues) corresponding to the type of the abnormal waveform.

As a result of the determination in step S08, if the comparison result is not within the normal range (step S08; No), the determination unit 110 reads, from the storage unit, an abnormality notification method according to the degree of the comparison result and the evaluation method.

(Step S10)

Based on the retrieved abnormality notification method, the determination unit 110 provides the notification of abnormality through the display unit 103 or the output unit 111. When the abnormality notification is provided on an external terminal device, the output unit 111 sends information on the abnormality to the external terminal device.

In the ultrasound diagnosis apparatus 100 of this embodiment, the evaluation value acquisition unit 107 captures images of the subject in the normal condition, and acquires the evaluation value of the function of the body tissues as a reference evaluation value. The evaluation value acquisition unit 107 acquires the evaluation values of the function based on ultrasound images obtained over time as compared evaluation values. The determination unit 110 compares the compared evaluation values with the reference evaluation value to determine whether each value is within the normal range. Having determined the value as being abnormal, the determination unit 110 reports the abnormality as a result of the determination. Thus, even if monitoring is performed for ultrasound examination for a certain period of time, the viewer of ultrasound images is not required to keep checking the images, or not required to refer to all the images generated over time.

Accordingly, it is possible to reduce the burden on the viewer of ultrasound images in ultrasound examination monitoring. Besides, the presence of abnormality is determined based on the evaluation value, and if there is abnormality, it is reported. As a result, the viewer of images can easily recognize the occurrence of abnormality. In view of the foregoing, the ultrasound diagnosis apparatus 100 of the embodiment enables the long-term monitoring of the conditions of body tissues. Further, it is possible to improve the efficiency of ultrasound examination.

The ultrasound diagnosis apparatus 100 of this embodiment includes the end part 10 having a structure in which the ultrasound transducer 12 is housed in the container 10a in a capsule form. The end part 10 is inserted in the subject's body. On the other hand, if a transesophageal echocardiography (TEE) probe is inserted in the esophagus, the guide tube portion form the grip to the end part stays in the esophagus. For example, when ultrasound waves are transmitted and received between a predetermined position in the esophagus and the heart, the guide tube portion is placed in the esophagus while at least ultrasound waves are being transmitted and received. That is, while an observation site such as the heart or the like is being monitored, the guide tube portion to the end part stays in the esophagus of the subject all the time.

The guide tube portion and the end part of the TEE probe are provided therein with not only a signal line for exchanging signals with the ultrasound transducer and a power supply or the like, but also a wire for bending the end part. This means that the subject is obliged to bear with patience the guide tube portion or the like that includes therein a wire and the like being placed in the esophagus. If the monitoring continues for a long time, it may impose a burden on the subject depending on his/her condition. As a result, the TEE probe may not be used for the continuous monitoring of the examination site. If ultrasound waves are transmitted and received at the outside of the body to avoid this problem, it is required to consider the influence of tissues present in the transmission/reception directions of ultrasound waves. As in the embodiment, if the end part 10 is in a capsule form, and only minimal lines such as a signal line and a power supply line are passed through the cable 11, it is possible to reduce the burden on the subject compared to the case of using the TEE probe.

<Modification>

Next, a modification of the first embodiment is described. In this modification, the transmitter/receiver unit 105 of the main body 101 implements the most functions of the transmitter 141 and the receiver 142 of the end part 10. With this, the internal structure of the container 10a may be simplified. Described below is an example of the functions of the transmitter/receiver unit 105.

(Transmitter Unit-Modification)

The transmitter unit of the transmitter/receiver unit 105 of the main body 101 includes a clock generation circuit, a transmitter delay circuit, and a pulser circuit (not illustrated), and the like, which are controlled by the main control unit 104. The clock generation circuit generates clock signals for determining the transmission frequency and the transmission timing of ultrasound waves. For example, the clock generation circuit feeds the transmitter delay circuit with a reference clock signal. The transmitter delay circuit sends the pulser circuit a drive signal having a predetermined delay time. The predetermined delay time is determined based on the transmission focal point of ultrasound waves. The pulser circuit includes therein as many pulsers as individual channels corresponding to the ultrasound oscillators 12a, and generates transmission drive pulses.

The pulser circuit repeatedly generates a rate pulse to form transmission ultrasound waves at a predetermined repetition frequency (PRF). The transmitter delay circuit provides the rate pulse with a delay time related to the transmission direction and the transmission focus. Transmission drive pulses are generated at timing based on the rate pulses each being delayed. The transmission drive pulses are sent to the end part 10 through the cable 11, and fed to the ultrasound oscillators 12a of the ultrasound transducer 12 via the transmit-receive controller 14. The transmission drive pulses excite the piezoelectric elements. As described above, the transmitter delay circuit provides the pulser circuit with a delay time to focus ultrasound waves for transmission, thereby converging the ultrasound waves into a beam. With this, the transmission directivity of the ultrasound waves is determined. In addition, the transmitter delay circuit changes the transmission delay time to be given to each rate pulse, thereby controlling the transmission direction of ultrasound wavefront.

(Receiver Unit-Modification)

The receiver unit of the transmitter/receiver unit 105 of the main body 101 receives echo signals corresponding to ultrasound waves reflected from the subject under the control of the main control unit 104. Having received the echo signals received by the end part 10, the receiver unit performs delay addition processing on them, thereby converting the analog echo signals to digital data having been subjected to phasing (i.e., subjected to beam forming). Specific examples are as follows.

The receiver unit of the transmitter/receiver unit 105 includes, for example, a preamplifier circuit, an A/D converter, a receiver delay circuit, and an adder (all not illustrated). The preamplifier circuit amplifies echo signals received from the ultrasound transducer 12 with respect to each receiver channel. The A/D converter converts the amplified echo signals to digital signals. Having been converted into digital signals, the echo signals are each stored in a digital memory. The digital memory is provided for each channel (or each element). Each echo signal is stored in the corresponding digital memory. The echo signal is also stored in an address corresponding to the time it is received.

The receiver delay circuit provides echo signals converted to digital signals with a delay time required to determine the reception directivity. The reception delay time is calculated for each element. The adder adds up the echo signals having the delay time. The adder reads each of the echo signals from the digital memory as appropriate based on the required delay time calculated, and adds up them. The adder repeats this addition while changing a reception focus position along the transmission beam. The addition emphasizes a reflection component from a direction corresponding to the reception directivity. The received beam signal processed by the receiver unit of the transmitter/receiver unit 105 is sent to the signal processor (the B-mode signal processing unit, the Doppler signal processing unit).

Second Embodiment

In the following, the ultrasound diagnosis apparatus 100 according to the second embodiment is described. In the first embodiment, based on anatomical images generated by the generating unit 109, evaluation values are obtained by an anatomical evaluation method. On the other hand, in the second embodiment, based on anatomical images generated by the generating unit 109, evaluation values are obtained by a functional evaluation method differently from the first embodiment. Otherwise, the ultrasound diagnosis apparatus 100 of the second embodiment is similar to that of the first embodiment. Only the differences are described below.

Described below are specific examples of the evaluation method performed by the evaluation value acquisition unit 107.

(Myocardial Strain Analysis; Evaluation Method Example 4)

Figure 13A:
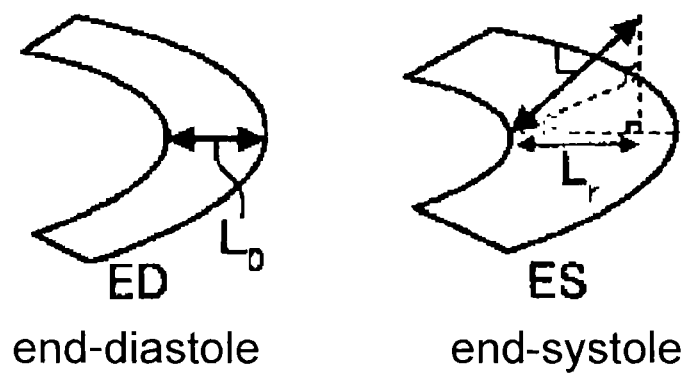
FIG. 13A is a schematic diagram illustrating an example (1) of evaluation index used in myocardial strain analysis.
Figure 13B:
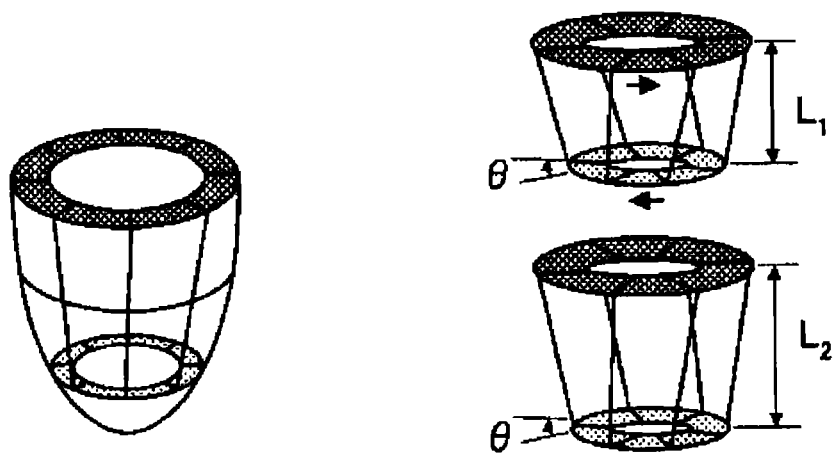
FIG. 13B is a schematic diagram illustrating an example (2) of evaluation index used in myocardial strain analysis.

The myocardial strain analysis performed by the evaluation value acquisition unit 107 is described with reference to FIGS. 13A and 13B. FIG. 13A is a schematic diagram illustrating an example (1) of evaluation index used in the myocardial strain analysis. FIG. 13B is a schematic diagram illustrating an example (2) of evaluation index used in the myocardial strain analysis. The "myocardial strain analysis" is one of the techniques for analyzing the heart wall motion to check expansion and contraction of the myocardium, and if twisting is normal or not. When the blood supply to the myocardium does not meet its demand, the muscle cannot expand and contract normally. As a result, the function of pumping blood to the body does not work properly. Through the myocardial strain analysis, such abnormality of the myocardium can be found.

<<Setting of Contour>>

The operator inserts the end part 10 in the subject's body to a predetermined position in the esophagus. Then, the operator adjusts the position of the ultrasound transducer 12 (rotate, tilt, etc.) or adjusts the ultrasound beam angle, so that the heart is included in ROI. With this, the display unit 103 displays a B-mode image representing a tomographic image of the heart. In the B-mode image of the heart, the main control unit 104 sets a contour at the boundary between the myocardium and the heart chamber (hereinafter, referred to as "myocardium/heart chamber boundary"). For example, the main control unit 104 extracts a contour corresponding to the boundary position in the cardiac cavity by manual setting of the operator, or by using an automatic method such as ACT (Automated-Contour-Tracking). This contour is used to detect the myocardium/heart chamber boundary.

Figure 14:
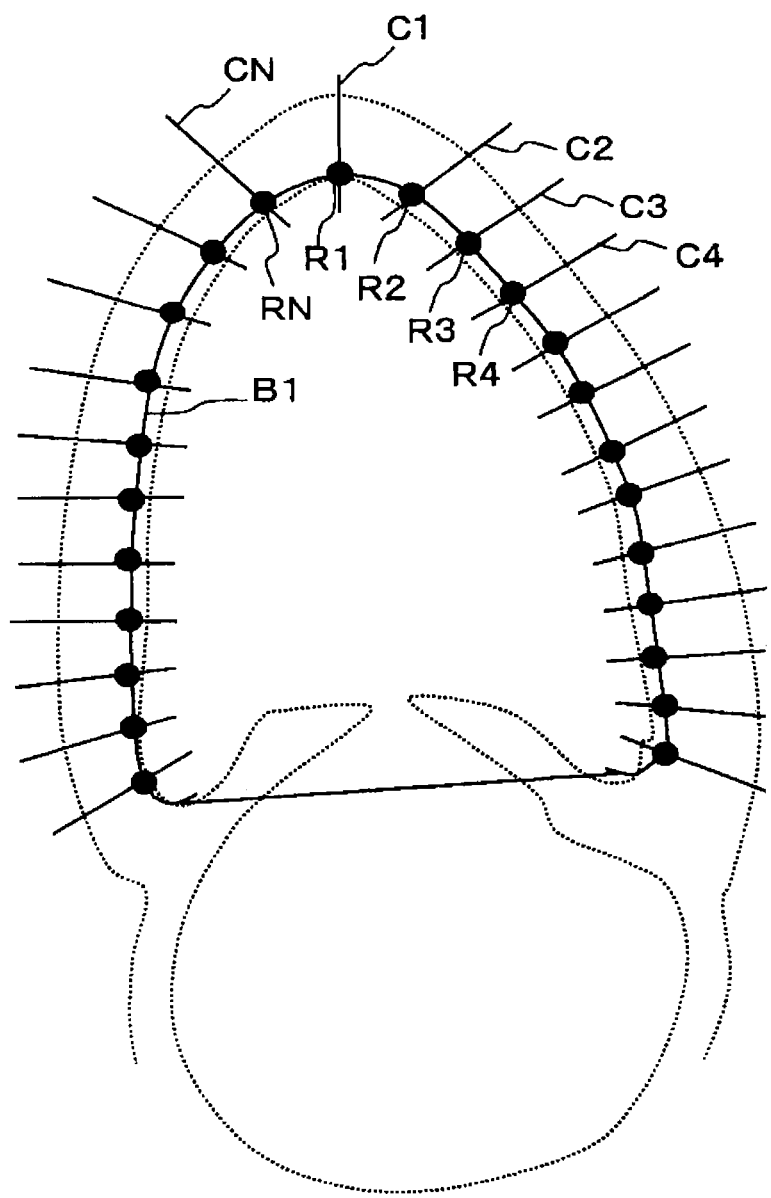
FIG. 14 is a schematic diagram illustrating a contour and operation points set on the apical two-chamber section.

A specific example of the contour setting is described with reference to FIG. 14. FIG. 14 is a schematic diagram illustrating a contour and operation points set on an apical two-chamber cross section. As illustrated in FIG. 14, the operator sets, through the operation unit 102, a closed curve B1 at a predetermined position in the heart chamber indicated on the tomographic image. As illustrated in FIG. 14, the main control unit 104 sets a plurality of operation points R1, R2, R3, . . . , RN on the closed curve at predetermined intervals. The main control unit 104 moves the operation points radially toward the myocardium. For example, the main control unit 104 moves the operation points R1, R2, R3, . . . , RN on the closed curve B1 along their normal directions C1, C2, C3, . . . , CN, respectively.

While moving the operation points RN, R1, R2, R3, . . . , RN radially, the main control unit 104 continuously obtains a pixel value in the tomographic image data corresponding to the position of each of the operation points R1, R2, R3, . . . , RN. Then, the main control unit 104 detects a boundary position between the myocardium and the heart chamber where the pixel value changes suddenly. Besides, the main control unit 104 generates contour data by connecting a plurality of boundary positions detected as above. In this generation of the contour data, the main control unit 104 sequentially retrieves pixel values of image data corresponding to the positions of the operation points R1, R2, R3, . . . , RN that radially move in the heart chamber, thereby obtaining the amount of change in pixel value. The main control unit 104 detects the boundary between the heart chamber in which reflection of ultrasound waves is small and the myocardium with relatively large reflection (myocardium/heart chamber boundary) based on the change amount.

<<Calculation of Radial Strain [%]>>

A description is given of the calculation of radial strain [%] by the evaluation value acquisition unit 107 with reference to FIGS. 13A and 13B. As illustrated in FIGS. 13A and 13B, the radial strain [%] is obtained by calculating the ratio of distance Lr between any two points in a line in the wall thickness direction in the end-systole to distance $L_0$ between the same two points in the wall thickness direction in the end-diastole (see formula (1) in FIG. 13A). 3D radial strain [%] is obtained by calculating the ratio of relative distance L between any two points in the end-systole to distance $L_0$ between the same two points in the end-diastole (see formula (2) in FIG. 13A).

<<Calculation of Twist and Torsion>>

Further, for example, as illustrated in FIG. 13B, the evaluation value acquisition unit 107 calculates the twist and torsion of the myocardium. The twist of the myocardium is calculated by obtaining difference θ in rotation angle caused by twisting between any two cross sections of the myocardium, for example, as illustrated in the left view of FIG. 13B. Besides, the torsion is a value obtained by normalizing the twist by distance L between any two cross sections of the myocardium, and calculated by Torsion=θ/L. Here, for example, as illustrated in the right view of FIG. 13B, even if difference θ is not generated in rotation angle between two cross sections, if distances $L_1$ and $L_2$ differ, there is a difference in the physical meaning of torsion.

(Calculation of Left Ventricular Ejection Fraction; Evaluation Method Example 5)

Described below is the calculation of left ventricular ejection fraction by the evaluation value acquisition unit 107. The evaluation value acquisition unit 107 stores heart chamber volume data obtained by the measurement of left ventricular volume as described above (evaluation method example 1 in the first embodiment) in the memory circuit thereof in association with cardiac time phase. From the heart chamber volume data, the evaluation value acquisition unit 107 reads heart chamber volume Vxs at end-systole and heart chamber volume Vxd at end-diastole, and calculates the cardiac ejection fraction Zx based on the following formula (4):

$$Zx=(Vxd-Vxs)/Vxd \times 100 (\%) \qquad (4)$$

With the ultrasound diagnosis apparatus 100 of this embodiment, even if monitoring is performed for ultrasound examination for a certain period of time, the viewer of ultrasound images is not required to keep checking the images, or not required to refer to all the images generated over time.

Accordingly, it is possible to reduce the burden on the viewer of ultrasound images in ultrasound examination monitoring. Besides, the presence of abnormality is determined based on the evaluation value, and if there is abnormality, it is reported. As a result, the viewer of images can easily recognize the occurrence of abnormality. In view of the foregoing, the ultrasound diagnosis apparatus 100 of the embodiment enables the long-term monitoring of the conditions of body tissues. Further, it is possible to improve the efficiency of ultrasound examination.

Moreover, the ultrasound diagnosis apparatus 100 is configured to acquire ultrasound images while looking for the right time to capture images, such as when there is a change in the conditions of the subject informed from the biological information measuring unit 120. That is, the ultrasound diagnosis apparatus 100 does not continue to acquire ultrasound images if the conditions of the subject are stable for a long period of time. As a result, the viewer of ultrasound images in the monitoring is not forced to examine unnecessary images. Thus, it is possible to reduce the burden on the viewer. This results in the improved efficiency of the ultrasound examination.

As in the first embodiment, the ultrasound diagnosis apparatus 100 of the second embodiment may have the end part 10 in a capsule form. Moreover, the end part 10 may have a structure in which only minimal lines such as a signal line and a power supply line are passed through the cable 11. This makes it possible to reduce the burden on the subject compared to the case of using the TEE probe.

Third Embodiment

In the following, the third embodiment is described. In the first and the second embodiments, evaluation values are obtained based on anatomical images generated by the generating unit 109. On the other hand, in the third embodiment, evaluation values are obtained based on Doppler waveform images generated by the generating unit 109 differently from the first and the second embodiments. Otherwise, the ultrasound diagnosis apparatus 100 of the third embodiment is similar to that of the first embodiment. Only the differences are described below.

<<Reference Evaluation Value>>

The generating unit 109 of the third embodiment generates Doppler waveform images such as Doppler spectrum images and the like based on Doppler signals obtained in the pulsed Doppler mode and the continuous wave Doppler mode. Having received a waveform image from the generating unit 109, the evaluation value acquisition unit 107 calculates the evaluation value (E/A ratio, etc.) of the waveform image (reference Doppler waveform) obtained when the subject is in the normal condition as in the first embodiment. The evaluation value is stored in the storage unit as a reference evaluation value.

<<Compared Evaluation Value>>

After calculating the reference evaluation value, the evaluation value acquisition unit 107 obtains a compared evaluation value by an evaluation method set in advance with respect to each of waveforms (compared Doppler waveforms) generated sequentially and over time by the generating unit 109. The abnormality determination and the abnormality notification are performed in a similar fashion as in the first embodiment by the determination unit 110. Therefore, the same description is not repeated.

(Measurement of Left Ventricular Inflow; Evaluation Method Example 6)

Described below is the overview of the measurement of left ventricular inflow and the evaluation of the function of body tissues using the measurement result performed by the evaluation value acquisition unit 107 in the third embodiment. Upon receipt of a Doppler waveform image from the generating unit 109, the evaluation value acquisition unit 107 traces the envelope of the waveform (curve defined by the peaks of the waveform) in real time. Thereby, the evaluation value acquisition unit 107 obtains the peak value (maximum amplitude) of the waveform in systole, the peak value of the waveform in early diastole, and the peak value of the waveform in end-diastole.

<<Functional Evaluation of Mitral Valve>>

As illustrated in FIG. 7B, when monitoring the left ventricular inflow that occurs during diastole, the evaluation value acquisition unit 107 detects the polarity of a waveform indicating the direction of the blood flow as negative (lower side in FIG. 7B). On the other hand, as illustrated in FIG. 7B, if reverse component (forward direction, upper side in FIG. 7B) is detected in systole, it means that there exists mitral regurgitation MR. Accordingly, having detected the polarity as negative in the detection of the peak value at systole, the evaluation value acquisition unit 107 determines the evaluation value as having been obtained when the subject is in the normal condition. That is, the evaluation value acquisition unit 107 uses this evaluation value as a reference evaluation value. On the other hand, if having detected reverse components (positive polarity, upper side in FIG. 7B) as the peak value at systole, this is determined as abnormal in the comparison result between the compared evaluation value and the reference evaluation value by the determination unit 110. Specifically, it is determined that mitral regurgitation (MR) exists, and abnormality notification is provided.

<<E/A Ratio>>

In the measurement of left ventricular inflow, the evaluation value acquisition unit 107 obtains the peak value of waveform in early diastole, i.e., E wave (early filling). In addition, the evaluation value acquisition unit 107 obtains the peak value of waveform in end-diastole, i.e., A wave (atrial filling). The evaluation value acquisition unit 107 obtains the ratio of the peak values of the E wave and the A wave. When cardiac function is normal, the E/A ratio is more than 1.0. Therefore, having obtained the E/A ratio, if the E/A ratio is more than 1.0, the evaluation value acquisition unit 107 determines the evaluation value as having been obtained when the subject is in the normal condition. That is, the evaluation value acquisition unit 107 uses this evaluation value as a reference evaluation value. On the other hand, if the E/A ratio obtained by the evaluation value acquisition unit 107 is less than 1.0, this is determined as abnormal in the comparison result between the compared evaluation value and the reference evaluation value by the determination unit 110. Specifically, it is determined that cardiac function has deteriorated, and abnormality notification is provided. For example, such notification as "left ventricular diastolic function deteriorates; Left ventricular inflow is mostly due to left atrial contraction", or the like is provided.

In the embodiment, Doppler waveform images generated by the generating unit 109 are an example of "Doppler waveform group". The "Doppler waveform group" includes "reference Doppler waveform" corresponding to "first anatomical image" and "compared Doppler waveform" corresponding to "second anatomical image" acquired after the "reference Doppler waveform".

With the ultrasound diagnosis apparatus 100 of this embodiment, even if monitoring is performed for ultrasound examination for a certain period of time, the viewer of ultrasound images is not required to keep checking the images, or not required to refer to all the images generated over time.

Accordingly, it is possible to reduce the burden on the viewer of ultrasound images in ultrasound examination monitoring. Besides, the presence of abnormality is determined based on the evaluation value, and if there is abnormality, it is reported. As a result, the viewer of images can easily recognize the occurrence of abnormality. In view of the foregoing, the ultrasound diagnosis apparatus 100 of the embodiment enables the long-term monitoring of the conditions of body tissues. Further, it is possible to improve the efficiency of ultrasound examination.

Moreover, the ultrasound diagnosis apparatus 100 is configured to acquire ultrasound images while looking for the right time to capture images, such as when there is a change in the conditions of the subject informed from the biological information measuring unit 120. That is, the ultrasound diagnosis apparatus 100 does not continue to acquire ultrasound images if the conditions of the subject are stable for a long period of time. As a result, the viewer of ultrasound images in the monitoring is not forced to examine unnecessary images. Thus, it is possible to reduce the burden on the viewer. This results in the improved efficiency of the ultrasound examination.

As in the first embodiment, the ultrasound diagnosis apparatus 100 of the third embodiment may have the end part 10 in a capsule form. Moreover, the end part 10 may have a structure in which only minimal lines such as a signal line and a power supply line are passed through the cable 11. This makes it possible to reduce the burden on the subject compared to the case of using the TEE probe.

Fourth Embodiment

In the following, the fourth embodiment is described. As described above, there are many different approaches to evaluate the function of body tissues of the subject. The abnormality indicated by, for example, myocardial strain analysis, left ventricular inflow, left atrial volume, left ventricular ejection fraction, ECG waveform, and the like appears in stages depending on the degree of deterioration of cardiac function. These evaluation methods are also different in the way to acquire data to be evaluated: evaluation based on anatomical images, based on Doppler waveforms, by analyzing ECG waveform, and the like. To acquire the data, i.e., perform ultrasound examination monitoring at a time imposes a work burden on the operator. According to the fourth embodiment, depending on the degree of deterioration in the function of body tissues of the subject, evaluation is made from various aspects, and abnormality notification is provided.

Described below is an example of the operation of the ultrasound diagnosis apparatus 100 of the fourth embodiment that performs a plurality of types of evaluation for the cardiac function.

<<Functional Evaluation of Mitral Valve>>

As the first step of ultrasound examination monitoring, the main control unit 104 of the ultrasound diagnosis apparatus 100 performs the functional evaluation of the mitral valve. The main control unit 104 makes the end part 10 transmit/receive ultrasound waves via the transmitter/receiver unit 105 to acquire, for example, Doppler waveform images in the pulsed Doppler mode. From waveforms of Doppler spectrum images generated by the generating unit 109, the evaluation value acquisition unit 107 measures peak values of waveforms in systole in the left ventricular inflow over time. The index of the monitoring is that the polarity of the peak value in systole is detected as positive (upper side), and the presence of mitral regurgitation is indicated by the detection.

<<Evaluation of Left Ventricular Diastolic Function>>

As the second step of ultrasound examination monitoring, the main control unit 104 of the ultrasound diagnosis apparatus 100 performs the functional evaluation of the left ventricular diastolic function. The main control unit 104 continues to acquire, for example, Doppler waveform images in the pulsed Doppler mode via the transmitter/receiver unit 105. From waveforms of Doppler spectrum images generated by the generating unit 109, the evaluation value acquisition unit 107 obtains peak values of waveforms (E wave, A wave) in early diastole and end-diastole in the left ventricular inflow. In addition, the evaluation value acquisition unit 107 obtains the E/A ratio. The evaluation value acquisition unit 107 measures peak values of waveforms in systole over time. The E/A ratio less than 1.0 indicates deterioration in left ventricular diastolic function.

The main control unit 104 switches the scan mode to a mode for acquiring anatomical images (B-mode images). Based on anatomical images generated by the generating unit 109, the evaluation value acquisition unit 107 measures the maximum left atrial diameter or the left atrial volume over time. A rapid increase in the maximum left atrial diameter or the left atrial volume indicates early heart failure.

<<Evaluation of Left Ventricular Ejection Fraction>>

As the third step of ultrasound examination monitoring, the main control unit 104 of the ultrasound diagnosis apparatus 100 evaluates the left ventricular ejection fraction. The main control unit 104 continues to acquire, for example, anatomical images via the transmitter/receiver unit 105 in a scan mode that allows the acquisition of anatomical images. The evaluation value acquisition unit 107 measures the heart chamber volume in each cardiac time phase, and stores it in the memory circuit (not illustrated) thereof with corresponding cardiac time phase as additional information. From heart chamber volume data stored in the memory circuit, the evaluation value acquisition unit 107 reads heart chamber volumes at end-systole and end-diastole, and calculates the cardiac ejection fraction. A sharp drop in left ventricular ejection fraction indicates mid-heart failure.

<<Evaluation of Stroke Volume>>

As the fourth step of ultrasound examination monitoring, the main control unit 104 of the ultrasound diagnosis apparatus 100 re-evaluates the left ventricular inflow. The main control unit 104 continues to acquire, for example, anatomical images via the transmitter/receiver unit 105 in a scan mode that allows the acquisition of anatomical images. The evaluation value acquisition unit 107 obtains a time-velocity integral TVI (correlating to the stroke volume) in systole based on anatomical images generated by the generating unit 109. The evaluation value acquisition unit 107 also obtains the aortic diameter D. The evaluation value acquisition unit 107 obtains a cross-sectional area using a predetermined formula (e.g., $(\pi D^2)/4$) based on the aorta diameter D. Further, the evaluation value acquisition unit 107 multiplies the cross-sectional area by the TVI value. Thereby the evaluation value acquisition unit 107 obtains the stroke volume. Incidentally, it is assumed that the aortic diameter D is constant during the monitoring. A sharp drop in stroke volume indicates end-stage heart failure.

According to this embodiment, the main control unit 104 performs in stages various types of monitoring for staged evaluation of the function of body tissues of the subject. That is, depending on the degree of deterioration in the function of body tissues of the subject, evaluation is made from various aspects, and abnormality notification is provided. This reduces the work burden on the operator and the viewer.

Fifth Embodiment

Figure 15:
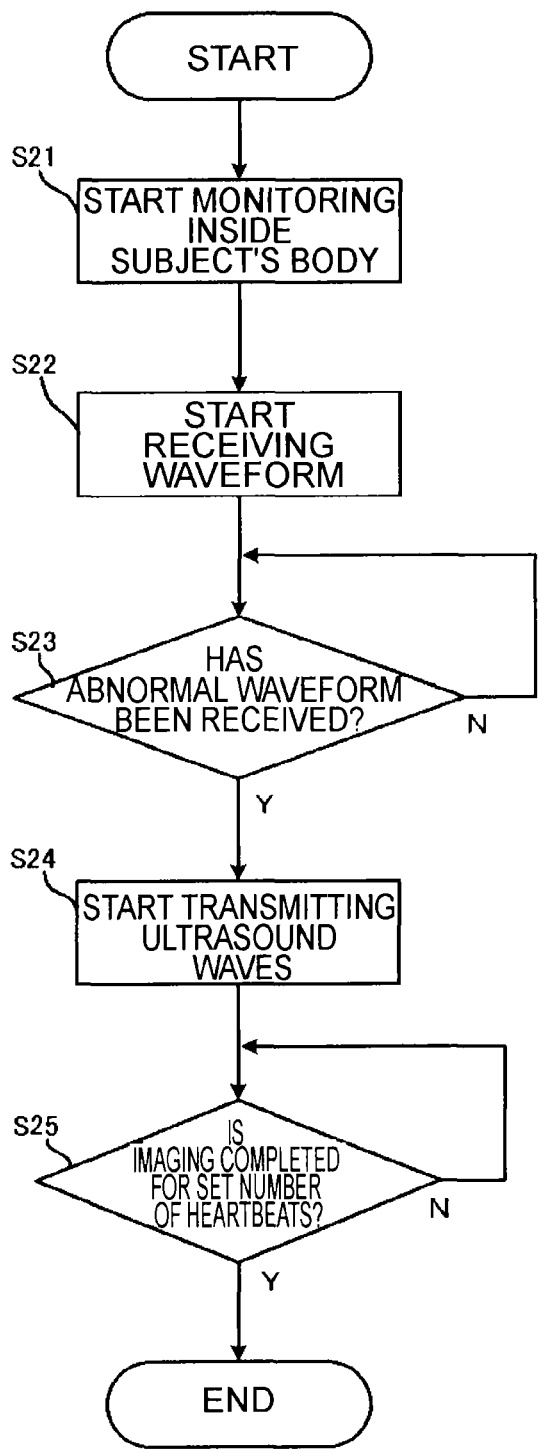
FIG. 15 is a flowchart schematically illustrating the operation of an ultrasound diagnosis apparatus according to a fifth embodiment.

In the following, the fifth embodiment is described. As described above, when the main control unit 104 performs in stages various types of monitoring for staged evaluation of the function of body tissues of the subject, the time taken for ultrasound examination monitoring is prolonged. Therefore, there is a need to suppress the excessive temperature rise of the end part 10 due to the heat generation of the ultrasound transducer 12. Referring to FIG. 15, the operation of the fifth embodiment that suppresses temperature rise is described. FIG. 15 is a flowchart schematically illustrating the operation of the ultrasound diagnosis apparatus 100 according to the fifth embodiment.
<Operation>
In the following, a description is given of a control flow to perform the intermittent imaging according to the embodiment with reference to FIG. 15.
(Step S21)
When the operator has determined the initial setting, the monitoring of body tissue is started. The initial setting is made through the operation unit 102, and includes selection of scan mode, settings of transmission focal point, sample volume, and the like. The initial setting also includes the condition where the biological information measuring unit 120 can obtain the biological information of the subject. For example, setting of ECG, setting of the analyzer of the biological information measuring unit 120, and the like are required. The initial setting further includes the condition where the end part 10 is inserted in the subject's body, and positions of the end part 10 and the tissue to be observed are adjusted. Besides, the operator sets the number of heartbeats as a reference for intermittently capturing ultrasound images.
(Step S22)
Having started measuring ECG waveform, the biological information measuring unit 120 sends the ECG waveform to the main control unit 104. Depending on the settings provided in advance in the biological information measuring unit 120, the biological information measuring unit 120 may send the main control unit 104 a specific ECG waveform (R wave, T wave, etc.) extracted by analyzing the obtained ECG waveform.
(Step S23)
The main control unit 104 determines whether an ECG waveform indicating abnormality (abnormality detection trigger) has been received from the biological information measuring unit 120. If, in step S23, determining that an abnormal ECG waveform has not been received (step S23; No), the main control unit 104 repeats this determination.
(Step S24)
In step S23, having determined that an abnormal ECG waveform has been received (step S23; Yes), the main control unit 104 sends a trigger signal to the transmitter/receiver unit 105. Upon receipt of the trigger signal, the transmitter/receiver unit 105 reads data of the number of heartbeats set in advance for the intermittent imaging from the storage unit (not illustrated). Having retrieved the data of the number of heartbeats, the transmitter/receiver unit 105 receives, from the main control unit 104, ECG waveform obtained in real time by the biological information measuring unit 120. Based on the real-time ECG waveform, the transmitter/receiver unit 105 makes the end part 10 start transmitting/receiving ultrasound waves according to the timing representing a specific waveform (R wave, etc.).
(Step S25)
When the end part 10 starts transmitting/receiving ultrasound waves in step S24, the receiver unit receives an echo signal, and the generating unit 109 generates an ultrasound image through several types of signal processing. Having started receiving ECG waveforms as well as transmitting ultrasound waves, the transmitter/receiver unit 105 starts measuring the timing to terminate the intermittent imaging from these time points. That is, the transmitter/receiver unit 105 determines whether the imaging is completed for the number of heartbeats set in advance based on, for example, ECG waveform received in real time. When the imaging has not yet been completed (step S25; No), the transmitter/receiver unit 105 repeats this determination.

For another example, the main control unit 104 may be configured to obtain the time taken for one heartbeat from ECG waveforms being received in real time. That is, the main control unit 104 obtains the imaging time for a predetermined number of heartbeats based on the time of one heartbeat. Having determined that the imaging for the predetermined number of heartbeats is completed, the main control unit 104 sends a trigger indicating the end of the imaging to the transmitter/receiver unit 105.

When determining that the intermittent imaging is completed (step S25; Yes), the transmitter/receiver unit 105 terminates the intermittent imaging without transmitting a signal related to the driving of the ultrasound transducer 12.

With the ultrasound diagnosis apparatus 100 of the fifth embodiment described above, the imaging is performed intermittently according to the periodic motion or conditions of body tissues of the subject. With this structure, ultrasound waves can be prevented from being transmitted continuously and all the time in the subject's body. Thus, it is possible to avoid heat generation due to the prolonged transmission of ultrasound waves.

Sixth Embodiment

Figure 16:
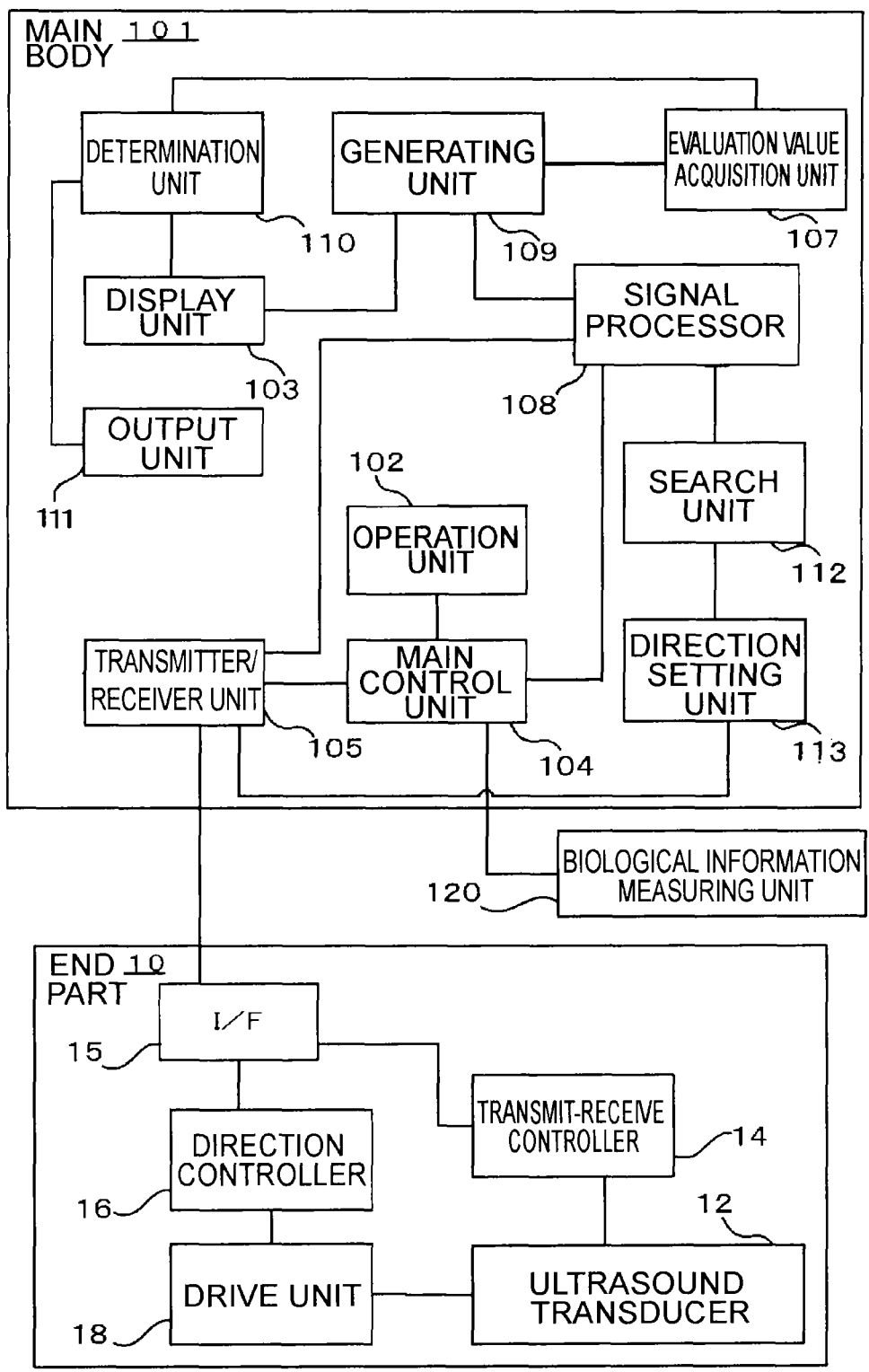
FIG. 16 is a schematic block diagram illustrating an example of the functional structure of a main body of an ultrasound diagnosis apparatus according to a sixth embodiment.

In the following, the sixth embodiment is described with reference to FIGS. 16 to 19. FIG. 16 is a schematic block diagram illustrating an example of the functional structure of a main body of an ultrasound diagnosis apparatus according to the sixth embodiment. As illustrated in FIG. 16, the main body 101 of the sixth embodiment includes a search unit 112.
(Direction Setting Unit)
The direction setting unit 113 of the embodiment receives transmission direction data from the search unit 112, and sets the transmission direction as well as performing the function described in the first embodiment. The details are described in the explanation of the search unit 112.

Incidentally, the direction setting unit 113 corresponds to an example of a "changer". Besides, in combination with the direction controller 16 and the drive unit 18 of the end part 10, the direction setting unit 113 corresponds to an example of a "changer". In combination with the transmitter/receiver unit 105 and the transmit-receive controller 14 of the end part 10, the direction setting unit 113 corresponds to an example of a "changer".

(Search Unit)

While the ultrasound diagnosis apparatus 100 is transmitting/receiving ultrasound waves to obtain an ultrasound image, for adjusting the transmission direction of the ultrasound waves and the position of an area to be examined, the search unit 112 searches for the transmission direction of the ultrasound waves. The search is based on a Doppler signal obtained by transmitting/receiving ultrasound waves in the Doppler mode. Specifically, the search is performed by determining whether the transmission direction of ultrasound waves in the Doppler signal (or sample volume) adjusts to the desired observation object that produces a blood flow. When the adjustment is performed by the search unit 112 as a precondition, if any scan mode is selected by the operator, the main control unit 104 controls the end part 10 to acquire the Doppler signal in parallel with the acquisition of the ultrasound image. Note that the Doppler signal indicates an echo signal obtained in the Doppler mode, or the RAW data of the Doppler image having subjected to the signal processing by the signal processor. For convenience of the description, the Doppler signal may be similarly described below. In addition, the Doppler mode indicates any one of scan modes for obtaining blood flow information, including pulsed Doppler mode, continuous wave Doppler mode, color Doppler mode, power Doppler mode, and the like. For convenience of the description, the Doppler mode may be similarly described below.

For example, while the B mode is selected and a B-mode image is generated, the main control unit 104 prompts the operator to set sample volume on the B-mode image BI displayed. When sample volume is set by the operator, according to a control signal received from the transmitter/receiver unit 105, the end part 10 alternately repeats B-mode scanning and the acquisition of Doppler signals in the pulsed Doppler mode. Based on the Doppler signals acquired, the search unit 112 performs the search process for the adjustment of the transmission direction of ultrasound waves and the position of an area to be examined. For example, the search unit 112 can be used to search for the transmission direction of ultrasound waves in the ultrasound transducer 12 upon monitoring cardiac ejection fraction.

Comparing pieces of signal strength information indicating the strength of Doppler signals obtained over time, the search unit 112 of the first mode determines the transmission direction of ultrasound waves with the highest signal strength. Described below is an example of the search process performed by the search unit 112.

<<Start of Transmission of Ultrasound Waves>>

After the end part 10 is inserted in the subject's body and scan mode is selected by the operator for preparation, the transmission of ultrasound waves is started. The receiver unit of the transmitter/receiver unit 105 of the main body 101 acquires echo signals based on the scan mode over time. The signal processor, the generating unit 109, and the like generate ultrasound images corresponding to the scan mode based on the echo signals. The display unit 103 displays the ultrasound images as appropriate. If the Doppler mode is selected as scan mode, only echo signals based on the selected scan mode are obtained. In other words, switching of the scan mode is not performed.

<<Start of Search>>

If the scan mode is the B mode, the signal processor (B-mode signal processing unit) sends RAW data based on the echo signals to the generating unit 109. The signal processor (Doppler signal processing unit) 108 sends Doppler signals to the search unit 112. The transmitter/receiver unit 105 of the main body 101 starts transmitting ultrasound waves in the Doppler mode for the search process of the search unit 112. Triggered by the elapse of a predetermined time (any time that is set) from the start of the transmission, the transmitter/receiver unit 105 makes the end part 10 transmit ultrasound waves in the Doppler mode. At this time, the direction setting unit 113 controls the end part 10 so that it transmits ultrasound waves not only in the direction in which ultrasound waves are transmitted first, but transmits ultrasound waves while changing the transmission direction. The time interval at which the search process is performed can be set arbitrarily.

<<Ultrasound Transmission Based on ECG Waveform>>

In the search process, ultrasound waves can be transmitted while the transmission direction is changed at any time interval set by the operator. For example, based on ECG waveform received from the biological information measuring unit 120, the main control unit 104 obtains predetermined cardiac time phase (diastole phase, etc.). The main control unit 104 may send the transmitter/receiver unit 105 a control signal related to the transmission timing of ultrasound waves with respect to each cardiac time phase thus obtained. The predetermined cardiac time phase refers to diastole or systole, early systole, mid-systole, end-systole, early diastole, mid-diastole, end-diastole or the like. Note that, in the search process, the main control unit 104 is not necessarily configured to transmit a control signal related to the transmission timing of ultrasound waves in the predetermined cardiac time phase. For another example, the main control unit 104 may be configured to obtain the predetermined cardiac time phase from ECG waveform received from the biological information measuring unit 120, and determine the signal strength (described later) of a Doppler signal corresponding to the predetermined cardiac time phase among Doppler signals acquired successively.

Also when the search unit 112 performs the search process, the initial setting of the Doppler mode is required. For example, the main control unit 104 notifies the operator of the start of selected scan mode, or prompts the operator to set sample volume before or after it. As the notification, for example, a predetermined character string may be displayed on the display unit 103, or voice guidance may be output. After a predetermined time has elapsed, first, the direction setting unit 113 makes the end part 10 transmit ultrasound waves via the transmitter/receiver unit 105 in the transmission direction corresponding to the initial setting. Then, the direction setting unit 113 makes the end part 10 transmit ultrasound waves via the transmitter/receiver unit 105 towards around the transmission direction of the initial setting, for example, in directions adjacent to the transmission direction of the initial setting.

<<Acquisition of Signal Strength Information>>

In the Doppler mode, the receiver unit of the transmitter/receiver unit 105 sequentially obtains Doppler signals transmitted in different directions. The Doppler signals are those obtained by the signal processor (Doppler signal processing unit) 108, and derived from blood flow (if the observation object is blood flow, blood flow PWD or CWD), or derived from tissues (if the observation object is tissues, tissue PWD). In the following, unless otherwise noted, the observation object is described as blood flow. In this case, it is assumed that a signal derived from blood flow, from which components derived from tissues that represent noise are removed, is extracted as a Doppler signal. The signal processor (Doppler signal processing unit) 108 sends a Doppler signal to the search unit 112. Together with information on the transmission direction of ultrasound waves, the search unit 112 stores Doppler signals obtained sequentially from the signal processor in a storage unit (not illustrated). From each of the stored Doppler signals transmitted in different directions, the search unit 112 acquires signal strength information that indicates the strength of the signal. The signal strength information is, for example, blood flow sensitivity information in the pulsed Doppler mode. In this case, the blood flow sensitivity information may be the amplitude value or the brightness value of a waveform depicted in a Doppler spectrum image. Each time the search unit 112 obtains a Doppler signal, the search unit 112 may acquire signal strength information from the Doppler signal. In this case, the search unit 112 stores, in the storage unit (not illustrated), signal strength information obtained sequentially and information on the transmission direction of ultrasound waves.

<<Comparison of Signal Strength>>

Besides, the search unit 112 compares Doppler signals in different directions corresponding to, for example, predetermined cardiac time phase, and obtains a Doppler signal having higher signal strength. By the comparison of signal strength, a Doppler signal indicating the highest signal strength is stored together with information on the corresponding transmission direction of ultrasound waves. The search unit 112 may acquire the signal strength upon acquisition of each Doppler signal. The search unit 112 may also be configured to obtain the highest signal strength from Doppler signals at each time point, after the completion of the search process described below.

<<End of Search>>

The transmission of ultrasound waves and the process of acquiring Doppler signals corresponding thereto continue, under the control of the direction setting unit 113, until a predetermined condition is satisfied. Examples of the predetermined condition include completion of predetermined times of transmission, completion of transmission in a predetermined range (a predetermined angle range from the sound source), elapse of a predetermined time, and the like. Upon receipt of a Doppler signal obtained last in a cycle, the search unit 112 obtains signal strength information determining that it is the end of the cycle. Then, the search unit 112 compares Doppler signals with a Doppler signal having the highest signal strength in an earlier cycle. With this comparison, the search unit 112 completes one cycle of the search process, and determines information on the transmission direction of ultrasound waves corresponding to a Doppler signal having the highest signal strength. The search unit 112 transmits the information on the transmission direction of ultrasound waves thus determined to the direction setting unit 113.

<<Update of Direction Setting>>

The direction setting unit 113 compares the information on the transmission direction of ultrasound waves received from the search unit 112 to the transmission direction of ultrasound waves before the search process. If there is a difference between them, based on the information on the transmission direction of ultrasound waves received from the search unit 112, the direction setting unit 113 updates the setting of the transmission direction of ultrasound waves. In addition, based on the updated setting, the direction setting unit 113 changes the transmission direction of ultrasound waves to a new direction through the transmitter 141 of the end part 10, or the direction controller 16 and the drive unit 18. The direction setting unit 113 and the search unit 112 of this embodiment correspond to an example of a "controller".

The above is an example of the search process by the search unit 112. As an another example, when the continuous wave Doppler mode is initially selected by the operator, the signal strength of a Doppler signal may be obtained in response to the start of the transmission of ultrasound waves without waiting for the elapse of a predetermined time as described above. In this case, changes in signal strength in the same transmission direction may be continuously obtained based on Doppler signals acquired sequentially. However, in the continuous wave Doppler mode, ultrasound waves are continuously transmitted and received. Therefore, it is preferable to search for the transmission direction of ultrasound waves as well as changing the transmission direction also at predetermined time intervals, in the same manner as the search of the transmission direction based on the signal strength as described above.

Due to the breathing, beats, body movement, throat reflection, emetic response, and the like of the subject, the transmission direction of ultrasound waves sometimes shifts from the object observed by the ultrasound diagnosis apparatus. In particular, if the observation object shifts not in the depth direction in the transmission direction of ultrasound waves, but in a direction deviating from the direction (orthogonal direction, etc.), it is difficult to continue the monitoring by the ultrasound diagnosis apparatus. Thus, each time a shift occurs, it is required to adjust the rotation and tilt of the ultrasound transducer 12 of the end part 10, the focus and transmission direction of ultrasound beams, and the like. Alternatively, each time a shift occurs, it is required to adjust the sample volume location (depth).

PWD mode has a range resolution. For example, during monitoring in the PWD mode, as well as the adjustment of the transmission direction of ultrasound beams, the sample volume location (depth) is adjusted with respect to the distance direction in the sound ray (scan line) of the ultrasound beams.

On the other hand, CWD mode has no range resolution. For example, during monitoring in the CWD mode, adjustment is performed for obtaining a location (depth) where the signal strength of a Doppler signal is the highest while the focus position (depth) of ultrasound beams is being changed.

However, it may be a heavy burden for the operator to keep monitoring shifts and also adjust them. If the operator bears these tasks, it may cause a decrease in the efficiency of monitoring inside the subject's body by the ultrasound diagnosis apparatus. In the case of long-term monitoring, since it is difficult for the operator to keep monitoring whether the transmission direction of ultrasound waves is appropriate, it may interfere with the implementation of the monitoring. In this respect, the ultrasound diagnosis apparatus 100 includes the search unit 112 as described above to periodically adjust the transmission direction of ultrasound waves, thus solving the problems. That is, it is possible to improve the operation efficiency without imposing burdensome tasks on the operator in monitoring inside the subject's body. Moreover, the ultrasound diagnosis apparatus 100 can effectively cope with long-term monitoring.

<Operation>

Figure 17:
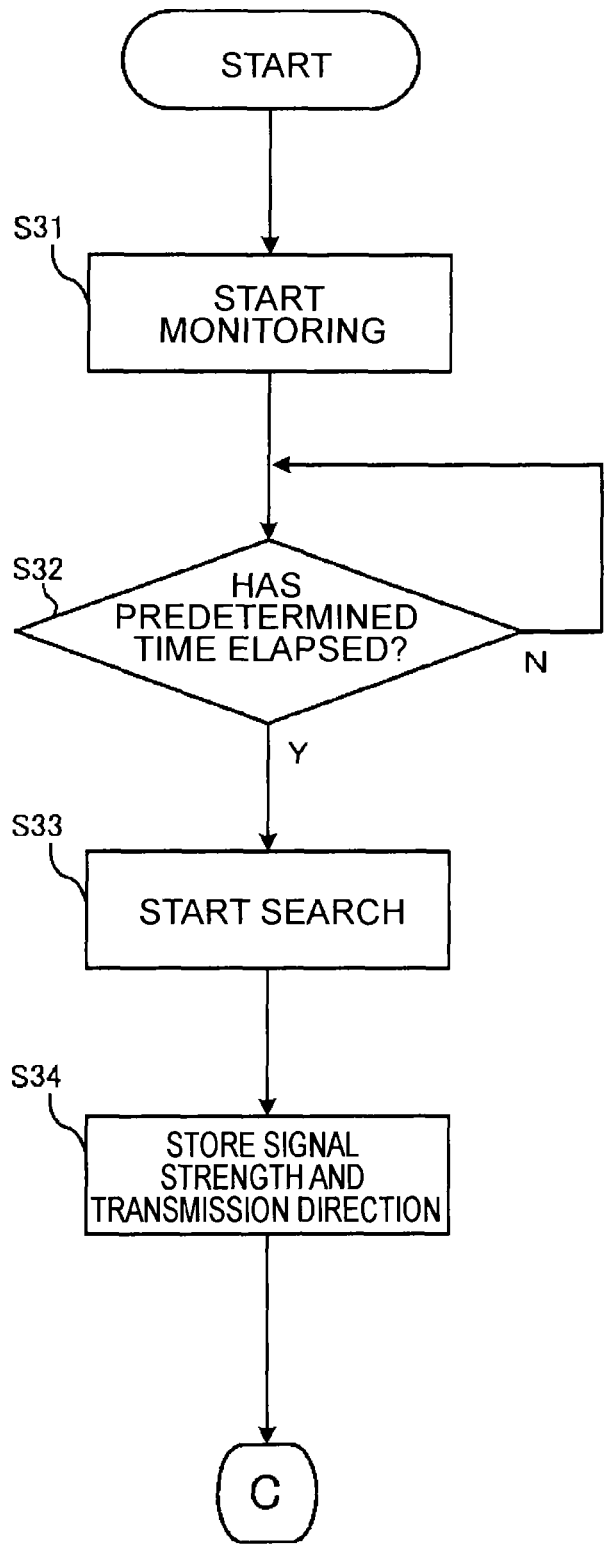
FIG. 17 is a flowchart schematically illustrating the operation of the ultrasound diagnosis apparatus of the sixth embodiment.
Figure 18:
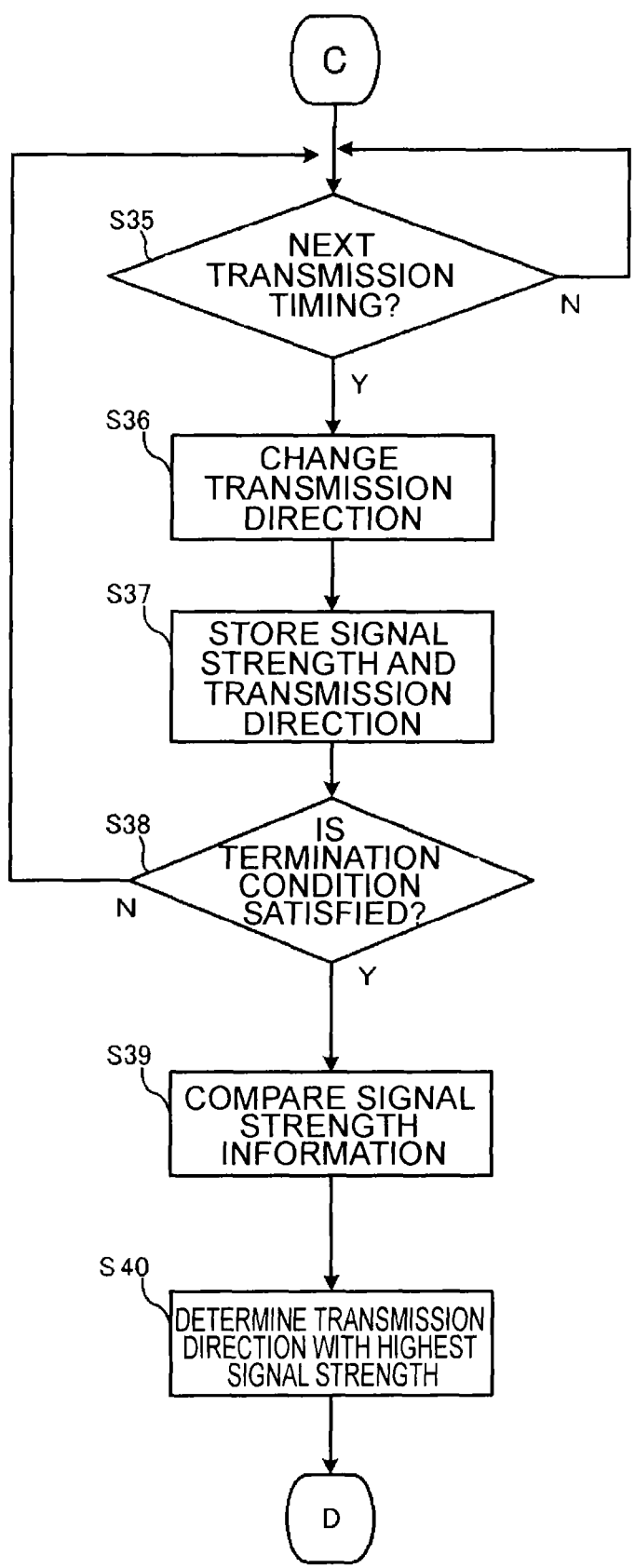
FIG. 18 is a flowchart schematically illustrating the operation of the ultrasound diagnosis apparatus of the sixth embodiment.
Figure 19:
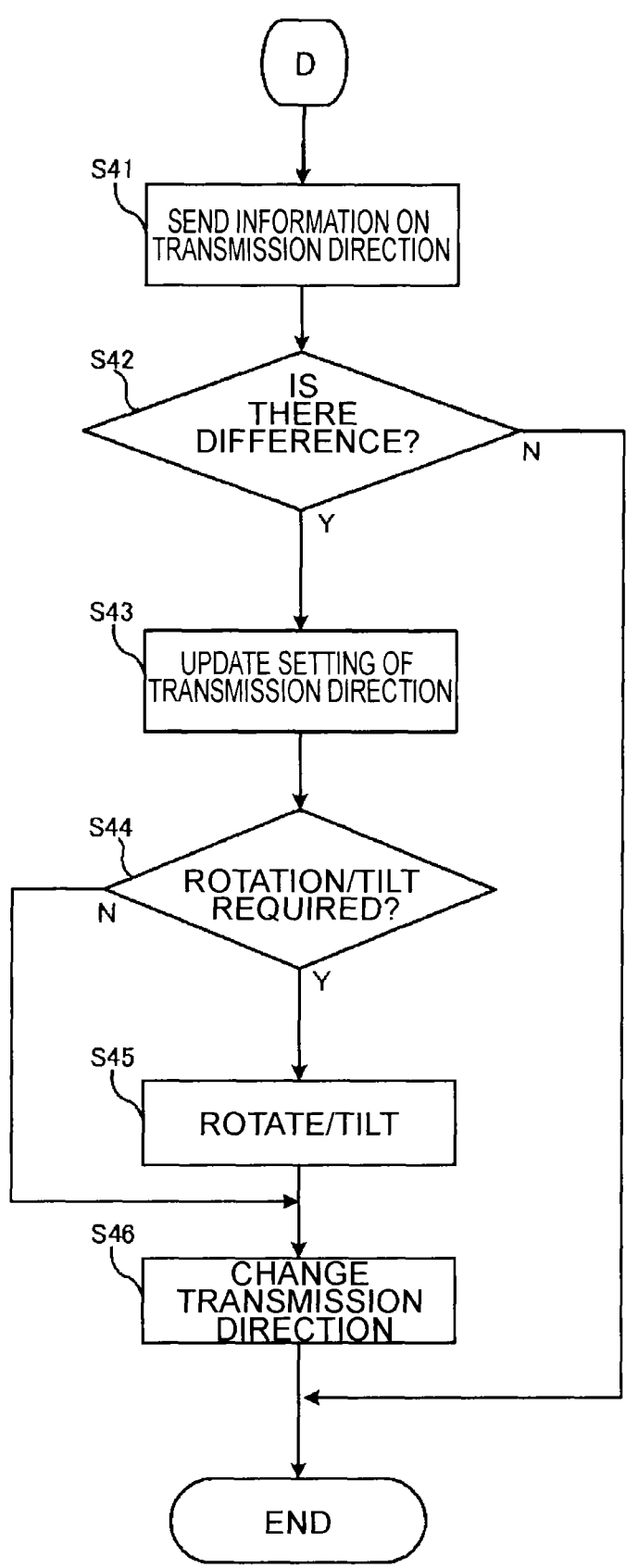
FIG. 19 is a flowchart schematically illustrating the operation of the ultrasound diagnosis apparatus of the sixth embodiment.

In the following, a description is given of a control flow to perform the search process at predetermined time intervals as well as displaying a B-mode image, a Doppler spectrum image, and ECG waveform in parallel according to the embodiment with reference to FIGS. 17 to 19. FIGS. 17 to 19 are flowcharts schematically illustrating the operation of the ultrasound diagnosis apparatus 100 of the sixth embodiment.

(Step S31)

When the operator determines the initial setting using the operation unit 102, the main control unit 104 controls the intermittent imaging as in the above embodiments.

(Step S32)

The main control unit 104 determines whether a predetermined time has elapsed from the start of the monitoring. If, in step S32, determining that the predetermined time (e.g., any time period set by the operator) has not elapsed (Step S32; No), the main control unit 104 repeats this determination.

(Step S33)

In step S32, having determined that the predetermined time has elapsed (Step S32; Yes), the main control unit 104 makes the end part 10 start transmitting/receiving ultrasound waves via the transmitter/receiver unit 105 for the search process. If a B-mode image BI is displayed on the display unit 103 (see FIG. 6), the main control unit 104 may prompt the operator to specify the position of sample volume. The operator specifies any region of the B-mode image BI as sample volume on the operation unit 102. In FIG. 6, the transmission direction is indicated by a broken line L1 extending from the left atrium LA through the mitral valve M to the left chamber, and passing by the center of the left heart. The specified sample volume is sent to the direction setting unit 113, and the direction setting unit 113 sends information on the transmission direction of ultrasound waves from the sound source to the end part 10 via the transmitter/receiver unit 105. The position of the sample volume may be specified prior to step S33.

(Step S34)

The transmitter/receiver unit 105 receives an echo signal based on the Doppler mode from the end part 10. The signal processor (Doppler signal processing unit) 108 performs the signal processing on the echo signal to obtain a Doppler signal and sends the Doppler signal to the search unit 112. The search unit 112 generates signal strength information based on the Doppler signal corresponding to predetermined cardiac time phase. The signal strength information generated by the search unit 112 is stored in the storage unit (not illustrated) with the information on the transmission direction of ultrasound waves.

(Step S35)

Based on the ECG waveform fed from the biological information measuring unit 120, the main control unit 104 measures the timing of the next transmission of ultrasound waves in the search process. The main control unit 104 repeats this (step S35; No) until the timing of the next transmission of ultrasound waves.

(Step S36)

In step S35, having determined that it is the timing of the next transmission of ultrasound waves based on the ECG waveform (step S35; Yes), the main control unit 104 controls the direction setting unit 113 so that the end part 10 transmits ultrasound waves after changing the transmission direction of ultrasound waves from the direction initially set to a direction around it. If the scan mode in the initial setting is not the Doppler mode, at the arrival of the time for transmitting ultrasound waves, the main control unit 104 changes the transmission direction of ultrasound waves by the direction setting unit 113 after switching the scan mode to the Doppler mode.

(Step S37)

Having received an echo signal related to ultrasound waves transmitted by changing the transmission direction, the receiver unit of the transmitter/receiver unit 105 sends the signal to the signal processor (Doppler signal processing unit) 108. The search unit 112 generates signal strength information based on the Doppler signal received from the signal processor (Doppler signal processing unit) 108, and stores it in the storage unit (not illustrated) with the information on the corresponding transmission direction of ultrasound waves. The main control unit 104 obtains the predetermined cardiac time phase based on the ECG waveform fed from the biological information measuring unit 120. The main control unit 104 also obtains signal strength corresponding to the predetermined cardiac time phase from among Doppler signals acquired successively.

(Step S38)

The main control unit 104 determines whether the termination condition of the search process, such as completion of predetermined times of transmission, completion of transmission in a predetermined range (a predetermined angle range from the sound source), elapse of a predetermined time, and the like, is satisfied. In step S38, having determined that the termination condition is not satisfied (step S38; No), the main control unit 104 repeats steps S35 to S38.

(Step S39)

In step S38, if the main control unit 104 determines that the termination condition of the search process is satisfied (step S38; Yes), the search unit 112 retrieves pieces of the signal strength information from the storage unit (not illustrated) and compares them. The search unit 112 may be configured to compare signal strength information with prior one each time signal strength information is obtained through the repetition of steps S35 to S37. In this case, since the provisional highest signal strength has already been determined, the search unit 112 compares signal strength obtained most recently with the provisional highest signal strength at the previous time.

(Step S40)

According to the result of the comparison in step S39, the search unit 112 determines the transmission direction of ultrasound waves with the highest signal strength.

(Step S41)

The search unit 112 sends the direction setting unit 113 information on the transmission direction of ultrasound waves thus determined.

(Step S42)

Comparing the transmission direction set in advance with the information on the transmission direction received in step S41, the direction setting unit 113 determines whether there is a difference between them.

(Step S43)

In step S42, having determined that there is a difference (step S42; Yes), the direction setting unit 113 updates the setting of the transmission direction of ultrasound waves based on the information on the transmission direction of ultrasound waves received in step S41.

(Step S44)

The direction setting unit 113 determines whether the ultrasound transducer 12 is required to be rotated or tilted by the direction controller 16 and the drive unit 18 based on the updated setting.

(Step S45)

In step S44, having determined that the ultrasound transducer 12 is required to be rotated or tilted (step S44; Yes), the direction setting unit 113 rotates or tilts the ultrasound transducer 12 with the direction controller 16 and the drive unit 18. However, when the 2D array ultrasound transducer 12 is used, there may be a case where this determination is not necessary.

(Step S46)

The direction setting unit 113 changes the transmission direction of ultrasound waves to a new direction for the monitoring by the intermittent imaging. In step S44, having determined that the ultrasound transducer 12 is not required to be rotated or tilted (step S44; No), the direction setting unit 113 performs this without performing step S45.

In step S42, having determined that there is no difference (step S42; No), the direction setting unit 113 ends the process without performing steps S43 to S46.

<Modification 1>

Described below is a modification 1 of the sixth embodiment. The ultrasound diagnosis apparatus 100 of the sixth embodiment is configured to search for the optimal transmission direction of ultrasound waves based on signal strength obtained by the search process. However, the sixth embodiment is not so limited. For example, the search unit 112 may perform the search process based on a waveform indicating blood flow information generated by the generating unit 109.

<<Generation of Reference Waveform Data>>

The second waveform data as a reference is stored in the storage unit (not illustrated). The second waveform is compared with the first waveform that is generated sequentially in the search process. The second waveform data is generated in advance, for example, at the start of monitoring, or before or after it. The second waveform data corresponds to predetermined cardiac time phase.

<<Start of Search>>

The transmitter/receiver unit 105 of the main body 101 starts transmitting ultrasound waves in the Doppler mode to obtain the first waveform used in the search process of the search unit 112. Triggered by the elapse of a predetermined time from when the second waveform is acquired, the transmitter/receiver unit 105 makes the end part 10 transmit ultrasound waves in the Doppler mode. The time interval at which the search process is performed can be set arbitrarily.

<<Ultrasound Transmission Based on ECG Waveform>>

In the search process, the time interval, at which ultrasound waves are transmitted while the transmission direction is changed, is set correspondingly to cardiac time phase in the second waveform.

<<Generation of Waveform Image>>

The signal processor (Doppler signal processing unit) 108 performs the same signal processing as in the sixth embodiment on echo signals received from the transmitter/receiver unit 105, thereby sending RAW data of Doppler spectrum images to the generating unit 109. The generating unit 109 sequentially generates Doppler spectrum images based on the RAW data. The waveform may be based on M-mode images (images collected in the M mode), provided that the first waveform and the second waveform are obtained in the same scan mode.

<<Generation of First Waveform>>

At this time, the main control unit 104 obtains cardiac time phase corresponding to that of the second waveform from the ECG waveform fed by the biological information measuring unit 120, and send it to the search unit 112. The search unit 112 extracts a waveform in the cardiac time phase corresponding to that of the second waveform from the waveform image generated by the generating unit 109. The search unit 112 uses this waveform as the first waveform.

<<Calculation of Similarity of Waveforms>>

The search unit 112 determines the similarity between the second waveform stored and each of the first waveforms generated sequentially in the search process. The similarity can be obtained by, for example, cross-correlation operation. When the overlapping area of the first waveform and the second waveform is at the peak, the search unit 112 determines it as representing high similarity, and obtains phase difference between the two at this time. The search unit 112 determines the similarity of the two waveforms based on the phase difference. The similarity information thus obtained is stored in the storage unit (not illustrated) with information on the transmission direction of ultrasound waves.

<<Comparison of Similarity>>

Comparing the first waveforms in different directions, the search unit 112 determines one which is more similar to the second waveform. The first waveform with the highest similarity in the comparison is stored with information on the corresponding transmission direction of ultrasound waves.

In this modification, the optimal transmission direction of ultrasound waves is searched for as described above. Regarding the transmission direction information, the direction setting unit 113 operates in the same manner as in the sixth embodiment. The modification 1 can be combined with the sixth embodiment.

The ultrasound diagnosis apparatus 100 of this embodiment transmits ultrasound waves at predetermined intervals in the transmission direction set in advance and directions around it, and acquires a plurality of Doppler signals corresponding to different transmission directions. The search unit 112 searches for the optimal transmission direction of ultrasound waves based on the Doppler signals. If a position shift has occurred, the direction setting unit 113 changes the transmission direction of ultrasound waves to the optimal transmission direction. Thus, even if the end part 10 shifts in the subject's body due to the breathing, beats, body movement, throat reflection, emetic response, and the like of the subject, and the transmission direction of ultrasound waves shifts from the object to be observed, it is possible to change the transmission direction of ultrasound waves to follow the shift, thereby enabling the continuation of monitoring inside the subject' body without imposing burdensome tasks on the operator. Moreover, even in long-term monitoring, it is possible to avoid a decrease in the operation efficiency.

Seventh Embodiment

In the following, the seventh embodiment is described. The ultrasound diagnosis apparatus 100 of the sixth embodiment is configured to search for the optimal transmission direction of ultrasound wave through the search process by the search unit 112. The seventh embodiment is the same in this respect. However, the search unit of the seventh embodiment further performs, when there is found no suitable transmission direction of ultrasound waves, error notification, termination of ultrasound monitoring (transmitting/receiving ultrasound waves), and the like. Otherwise, the ultrasound diagnosis apparatus 100 of the seventh embodiment is similar to that of the sixth embodiment. Only the differences are described below.

(Search Process—Signal Strength)

The search unit 112 of the seventh embodiment stores a threshold for signal strength. In the search process, having determined the highest signal strength, the search unit 112 compares the signal strength with the threshold. If the signal strength is below the threshold, the search unit 112 determines that there is found no suitable transmission direction of ultrasound waves. Then, the search unit 112 notifies, via a notification unit (not illustrated), the operator of recognizable error information. For example, the notification unit displays an error message on the display unit 103. For another example, the notification unit outputs predetermined sound from an audio output unit (not illustrated). In this case, the search unit 112 does not send information on the transmission direction of ultrasound waves to the direction setting unit 113.

As another operation of the search unit 112, if the signal strength is below the threshold, the search unit 112 determines that there is found no suitable transmission direction of ultrasound waves. Then, the search unit 112 informs the main control unit 104 of this. Upon receipt of the information, the main control unit 104 stops the transmission of ultrasound waves by the end part 10. As an example of the situation where the search unit 112 cannot find the suitable transmission direction of ultrasound waves may be cited a case where the shift of the end part 10 is large. In this case, the observation object is likely to be not included in ROI even if the direction setting unit 113 rotates/tilts the ultrasound transducer 12 and changes the transmission direction of ultrasound waves by electronic scanning.

(Search Process—Similarity)

The search unit 112 of the seventh embodiment stores a threshold for similarity. In the search process, having determined the transmission direction of ultrasound waves with the highest similarity, the search unit 112 compares the similarity with the threshold. If the similarity is below the threshold, the search unit 112 determines that there is found no suitable transmission direction of ultrasound waves. Then, the search unit 112 notifies, via the notification unit (not illustrated), the operator of recognizable error information. The notification unit operates in the same manner as described above. Also, the main control unit 104 stops the transmission of ultrasound waves by the end part 10 in the same manner as described above.

In this embodiment, the ultrasound diagnosis apparatus 100 is configured to perform, when there is found no optimal transmission direction of ultrasound waves, error notification, termination of ultrasound transmission, and the like. For example, if the observation object is not included in ROI even by rotating/tilting the ultrasound transducer 12 and changing the transmission direction of ultrasound waves by electronic scanning, the operator needs to recognize the situation. In addition, the end part 10 is required to be removed in such a situation. In this respect, according to the embodiment, even when the end part 10 has shifted largely with respect to the subject, the operator can handle the situation appropriately.

The first to the seventh embodiments can be used in any combination as appropriate. In the embodiments, not only the end part 10 in a capsule form, but a TEE probe may also be used.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
    an ultrasound transducer configured to transmit and receive ultrasound waves while being placed in an esophagus of a subject, to sequentially acquire cardiac function information of a heart of the subject; and
    processing circuitry configured to
        generate an image group over time based on the cardiac function information sequentially acquired;
        obtain an evaluation value for evaluating a function of tissue including the predetermined site based on the generated image group;
        determine whether the function of the tissue is abnormal, based on the evaluation value; and
        output information based on a result of the determination, wherein the processing circuitry is further configured to
        obtain, for the subject, a first image of a normal condition,
        obtain, for the subject, a reference evaluation value based on the first image of a normal condition,
        obtain, for the subject, a second image acquired after the first image,
        obtain, for the subject, a new evaluation value as a second evaluation value based on the second image,
        compare, for the subject, the second evaluation value with the reference evaluation value to determine whether the function of the tissue corresponding to the second evaluation value of the second image is abnormal, and
        repeat the obtaining of the second image, the obtaining of the second evaluation value, and the comparing of the second evaluation value to the reference evaluation value, for a sequence of second images.

2. The ultrasound diagnosis apparatus according to claim 1, wherein the processing circuitry is further configured to determine whether a difference between the second evaluation value and the reference evaluation value is within a predetermined range.

3. The ultrasound diagnosis apparatus according to claim 2, wherein each image is an anatomical image and the processing circuitry is further configured to obtain the reference evaluation value and the second evaluation values based on an anatomical evaluation of each anatomical image.

4. The ultrasound diagnosis apparatus according to claim 2, wherein each image is an anatomical image and the processing circuitry is further configured to obtain the reference evaluation value and the second evaluation values based on a functional evaluation of the tissue in each anatomical image.

5. The ultrasound diagnosis apparatus according to claim 1, wherein the processing circuitry is further configured to obtain the evaluation value from a Doppler waveform based on the cardiac function information.

6. The ultrasound diagnosis apparatus according to claim 5, further comprising a generator configured to generate a Doppler waveform group over time based on the biological information sequentially acquired, wherein
    the Doppler waveform group includes a reference Doppler waveform, and compared Doppler waveforms acquired after the reference Doppler waveform, and
    the processing circuitry is further configured to
        obtain the reference evaluation value based on the reference Doppler waveform, and sequentially obtain the second evaluation values each based on one of the compared Doppler waveforms generated over time, and
        compare each one of the second evaluation values with the reference evaluation value to determine whether the function corresponding to the one of the second evaluation values is abnormal.

7. The ultrasound diagnosis apparatus according to claim 6, wherein the processing circuitry is further configured to determine whether a difference between each of the second evaluation values and the reference evaluation value is within a predetermined range.

8. The ultrasound diagnosis apparatus according to claim 1, wherein the processing circuitry is further configured to switch at least one of a transmission method of the ultrasound waves by the ultrasound transducer, a type of image to be generated, and an evaluation method used, to measure a plurality of types of functions of the tissue.

9. The ultrasound diagnosis apparatus according to claim 1, wherein the ultrasound transducer is configured to be included in a container in a capsule form, and
the container further includes
an interface configured to transmit and receive signals between the ultrasound transducer and a main body that is an external device with respect to the container; and
a power supply line configured to supply power to at least the ultrasound transducer.

10. The ultrasound diagnosis apparatus according to claim 1, further comprising a container in a capsule form, the container including:
the ultrasound transducer;
an interface configured to transmit and receive signals between the ultrasound transducer and a main body; and
a power supply line configured to supply power to at least the ultrasound transducer.

11. The ultrasound diagnosis apparatus according to claim 9, wherein
the main body includes a signal processor connected to the interface and a power supply connected to the power supply line, and configured to perform signal processing on signals based on the cardiac function information received from the ultrasound transducer, and
the container is configured to be connected to the main body by the interface.

12. The ultrasound diagnosis apparatus according to claim 10, wherein
the main body includes a signal processor connected to the interface and a power supply connected to the power supply line, and configured to perform signal processing on signals based on the cardiac function information received from the ultrasound transducer, and
the container is configured to be connected to the main body by the interface.

13. The ultrasound diagnosis apparatus according to claim 9, wherein the container is configured to be placed in the esophagus of the subject.

14. The ultrasound diagnosis apparatus according to claim 11, wherein the container is configured to be placed in the tissue esophagus of the subject.

* * * * *